(12) United States Patent
Van Doorn et al.

(10) Patent No.: US 8,563,324 B2
(45) Date of Patent: Oct. 22, 2013

(54) DEVICE AND METHOD FOR IRRADIATING A SAMPLE WITH FOCUSED ACOUSTIC ENERGY INCLUDING A FULLY SOLID COUPLER

(75) Inventors: Arie R. Van Doorn, Eindhoven (NL); Ronald De Gier, Eindhoven (NL); Louis Stroucken, Eindhoven (NL); Marloes M. E. B. Van De Wal, Eindhoven (NL); Sergei Shulepov, Eindhoven (NL); Nicolaas B. Roozen, Eindhoven (NL); Contantijn W. M. Brantjes, Eindhoven (NL); Hendrik S. Van Damme, Eindhoven (NL); Michiel de Jong, Eindhoven (NL)

(73) Assignee: Biocartis SA, Lausanne (CH)

( * ) Notice: Subject to any disclaimer, the term of this patent is extended or adjusted under 35 U.S.C. 154(b) by 0 days.

(21) Appl. No.: 13/273,677

(22) Filed: Oct. 14, 2011

(65) Prior Publication Data

US 2012/0088310 A1   Apr. 12, 2012
US 2013/0230930 A2   Sep. 5, 2013

Related U.S. Application Data

(63) Continuation of application No. PCT/CH2010/000093, filed on Apr. 9, 2010.

(30) Foreign Application Priority Data

Apr. 14, 2009   (EP) ...................................... 09157850

(51) Int. Cl.
 *G01N 1/00*   (2006.01)

(52) U.S. Cl.
USPC .............. 436/174; 422/50; 422/500; 422/536

(58) Field of Classification Search
USPC .......... 422/50, 536, 500; 436/174; 435/306.1, 435/283.1, 259
See application file for complete search history.

(56) References Cited

U.S. PATENT DOCUMENTS 4,102,185 A * 7/1978 Dowling et al. ........... 73/152.05

(Continued)

FOREIGN PATENT DOCUMENTS

| JP | 2007-10345 A | 1/2007 |
| WO | 9619301 A1 | 6/1996 |
| WO | 2007016605 A2 | 2/2007 |

OTHER PUBLICATIONS

Hadimioglu, B. et al. "Polymer films as acoustic matching layers." Ultrasonics Symposium (1990) 1337-1340.*

(Continued)

*Primary Examiner* — Yelena G Gakh
*Assistant Examiner* — Christopher A Hixson
(74) *Attorney, Agent, or Firm* — Kusner & Jaffe

(57) ABSTRACT

A device for receiving a sample carrier is provided. The device includes an opening for receiving part of the sample carrier and a cutter for removing a part of the sample carrier. The cutter is coupled to a lid, which is movable to allow the cutter to make an incision in the sample carrier and, at the same time, to close at least part of the opening left open after receipt of the sample carrier. The disclosure further relates to a system comprising such a device and a method for operating such a device.

14 Claims, 13 Drawing Sheets

(56) References Cited

U.S. PATENT DOCUMENTS

| | | |
|---|---|---|
| 6,318,158 B1 | 11/2001 | Breen et al. |
| 6,699,711 B1 | 3/2004 | Hahn et al. |
| 2006/0094028 A1 | 5/2006 | Danna et al. |
| 2007/0002678 A1* | 1/2007 | Murakami .................... 366/116 |

OTHER PUBLICATIONS

Martin, Stephen J. et al. "Dynamics and response of polmyer-coated surface acoustic wave devices: Effect of viscoelastic properties and film resonance." Analytical Chemistry (1994) 66 2201-2219.*

International Search Report dated Jul. 26, 2010 from PCT/CH2010/000093.

* cited by examiner

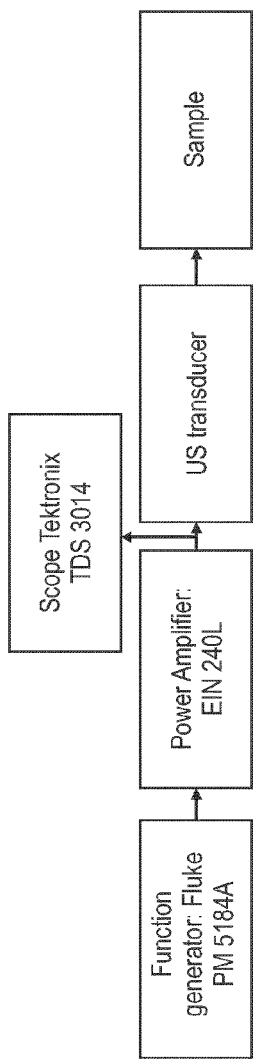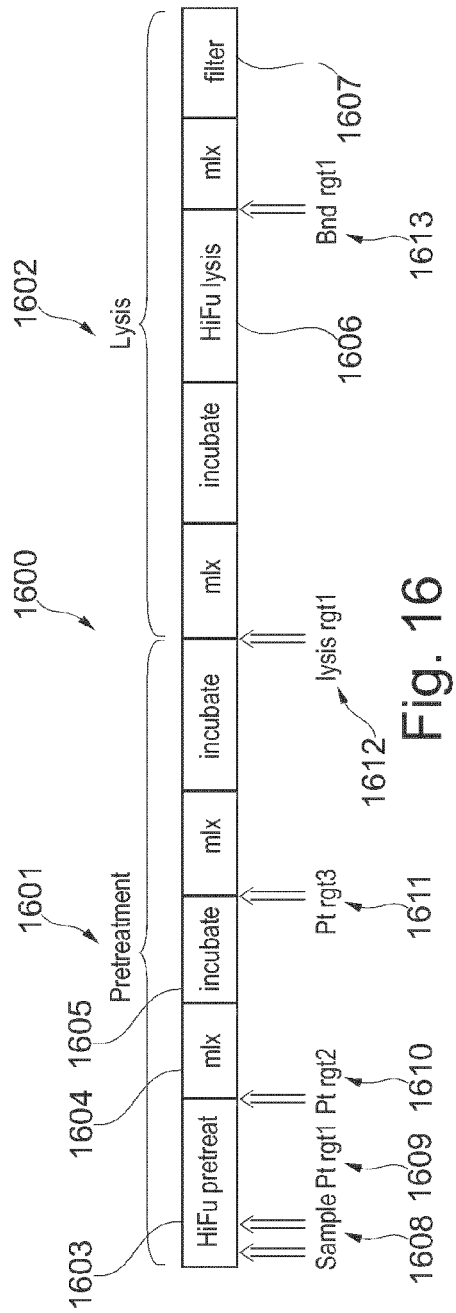

DEVICE AND METHOD FOR IRRADIATING A SAMPLE WITH FOCUSED ACOUSTIC ENERGY INCLUDING A FULLY SOLID COUPLER

CROSS REFERENCE TO RELATED APPLICATIONS

This application is a continuation of International Application No. PCT/CH2010/000093 filed Apr. 9, 2010, now pending, which claims the benefit under 35 U.S.C. §119(a) of European Patent Application No. 09157850.0, filed Apr. 14, 2009, the entire contents of both of which are incorporated herein by reference.

BACKGROUND OF THE INVENTION

1. Field of the Invention

The present invention relates to the treatment of samples with focused acoustic energy. In particular the invention relates to a device for irradiating a sample with focused acoustic energy to treat the sample and a method for irradiating a sample with focused acoustic energy to treat the sample.

2. Description of Related Art

In recent years progress in many aspects of sample-in result-out devices, also known as micro total analysis systems (microTAS) or lab-on-a-chip, has generated, for a variety of reasons, an increasing interest in in-vitro-diagnostic (IVD) applications. For example the integration and miniaturization results in systems requiring a relative small, acceptable contamination risk of the sample, high sensitivity and short turn-around time of the test and lower costs per test. Furthermore between sample-input and result generation minimal operator intervention shall be required. Operator interventions can be done by relatively unskilled operators and moderate demands on operating environment.

Known technologies of treating samples with acoustic energy may not be appropriate for certain applications like molecular device applications because after completion of the sonic treatment no distinction may be made between a leaking cartridge having a liquid sample inside and the liquid being used by the device itself. That may be a non-acceptable treatment result within these devices using such a liquid-coupling.

Furthermore the pretreatment function including complex operations like e.g. mixing, is processed separately and independently from other processing functions. This is opposite to the general trend in this domain of further miniaturization and integration. Even more seriously, it contradicts with for example hospital or lab requirements to have real small size systems, because of the very limited space available in these settings.

In addition to that molecular diagnostic tests often include technologies with complicated piezo arrays, complicated control systems and complicated electric drivers. These technologies are expensive, require a lot of technical support and also need much space.

SUMMARY OF THE INVENTION

It may be an object of the invention to provide for an improved treatment of samples.

Definitions and abbreviations: It shall be noted that in the context of this invention the following definitions and abbreviations will be used:

Dry coupling: The term "dry coupling" will be used in the context of the invention as a complete transmission of the acoustic energy through only non-liquid matter from the source to the sample.

Acoustic energy: The term "acoustic energy" is in the context of the invention used as comprising such terms as sonic energy, acoustic waves, acoustic pulses, ultrasonic energy, ultrasonic waves, ultrasound, shockwaves, sound energy, sound waves, sonic pulses, pulses, waves or any other grammatical form of these terms.

Focal region and focal point: "Focal region" or "focal point" as used in the context of the present invention means that a region where the acoustic energy converges and/or hits a target or sample, although that region has not necessarily to be a single focused point.

Device: The expression "device" in the context of the invention includes molecular diagnostic devices as well as other devices. Applications of the device may e.g. be in healthcare/life science, food industry, veterinary practice and forensic applications.

Sample: It shall explicitly be noted that the term "sample" may contain samples for molecular analysis being treated with the device according to the present invention. For example blood, cultured blood, urine, aspirate, samples with water like viscosity, heterogeneous samples or samples on a carrier like BAL, sputum, tracheal aspirate, CSF, swab and/or brush with pathogen. Nevertheless this does not mean that any other kind of matter, solid, liquid, gaseous or any combination thereof is excluded from being a sample and being irradiated with focused acoustic energy by the invention.

NA: "NA" will be used for any nucleic acid.

Source: In the context of the invention the term "source" will be used synonymously to the term transducer. Additionally any other apparatus that is able to emit acoustic energy as defined within the context of the invention is comprised in the source.

Propagation path: The expression "propagation path" describes in the context of the invention the way of the acoustic energy from the source through any combination of at least the coupler and the cartridge to the sample. Other elements like lenses, additional couplers may be in the propagation path. Thus in the propagation path also the intermediate contact layers of these different elements are passed by the acoustic energy. Additionally other layers like e.g. the acoustic window or the interface medium may be comprised.

Attenuation: The term "attenuation" in the context of the invention relates to a decrease of the intensity of the generated acoustic energy. This may be e.g. due to reflection, absorption, diffraction, or any combination thereof.

Treatment of the sample: The term "treatment" or "treating" is used in the context of the invention to describe the interaction of the focused acoustic energy with the sample. By means of focusing the acoustic energy onto the sample in various specific ways sonochemical and/or sonophysical reactions are caused in the sample to generate functionalities like e.g. mixing, dispersing, stirring, elution from swabs or brushes, liquefaction, lysing or cell release. Thereby this definition of "treatment" also describes the sonophysical and/or the sonochemical interactions during the process called "pretreatment". In other words "treatment" comprises amongst other functionalities the "pretreatment" of a sample.

Process chamber: The expression "process chamber" will be similarly used to "chamber" and "chamber of the cartridge".

Ultrasound: The terms "ultrasound" and "ultrasonic" will be used for cyclic sound pressure with a frequency between 20 kHz and 100 kHz.

High Intensity Focused Ultrasound (HiFu): The term "HiFu" will be used in the context of the invention as focused acoustic field with source frequencies in the range of 0.2 MHz to 10 Mhz, with amplitudes chosen to be sufficient efficient to create high pressure shock-waves and/or cavitation in the focal zone. Focal zone dimensions (length and diameter) are dependent on the source transducer type (e.g. natural focusing by flat or enforced focusing by conical/spherical source transducers). Exemplary length-scales for the indicated frequency range are (sub) millimeters.

Sample-in result out-system: A system which accepts a (e.g. biological) sample, does all the required preparation steps to prepare for detecting any kind of facts, runs the detection and delivers the detection results. For example a device for molecular analysis of samples like e.g. blood or other cells can be provided, that provides for all necessary analysis steps from the supply of the natural, untreated sample to the result of the analysis.

Lens: In the context of the present invention the term "lens" may be used as a component or a system that is enabled to spread or converge acoustic energy. Any matter being able to influence the propagation characteristics of the generated acoustic energy shall be included within the term "lens".

Interface/Interface medium: In the context of the invention the propagation path of the acoustic energy may comprise several components like the source, the full solid coupler and the cartridge. In order to describe the transitions or areas where these different elements of the propagation path get in physical contact to each other the terms interface and interface medium are used. For example if a coupler is physically contacted with the cartridge, the interface medium of the coupler describes the material used in the coupler within this area of the coupler brought in contact with the cartridge.

Coupler: The term coupler will be used in the context of the invention as an element that is part of the propagation path of the acoustic energy and transfers may be with other elements the acoustic energy from the source to the cartridge. Furthermore the term coupler will be used similarly to the term full solid coupler.

Solid gel: In the context of the present invention "solid gel" comprises a gel-forming material only. It is fully solid and it is at the same time a gel. Liquid substances are fully avoided within a solid gel. Thus water or hydrogel is avoided when using a solid gel. Thus the term "gel" is similarly used in the context of the invention to the term "solid gel".

It should be noted that embodiments described in the following similarly pertain to the device for irradiating a sample with focused acoustic energy and the method for irradiating a sample with focused acoustic energy. Synergetic effects may arise from different combinations of the embodiments although they might not be described explicitly or in detail.

Further on, it shall be noted that all embodiments of the present invention concerning a method, may be carried out with the order of the steps as described, nevertheless this has not to be the only and essential order of the steps of the method. All different orders and combinations of the method steps are herewith disclosed.

According to a first aspect of the present invention, there is provided a full solid coupler for a complete dry coupling of acoustic energy between a source and a cartridge. Accordingly, in a first exemplary embodiment of the invention a device for irradiating a sample with focused acoustic energy to treat the sample is presented, wherein the device comprises an instrument, a cartridge, a full solid coupler and a source for generating the acoustic energy. Furthermore the cartridge has a chamber for receiving the sample and the full solid coupler provides a complete dry coupling of the acoustic energy between the source and the cartridge. The instrument and the cartridge are adapted for inserting the cartridge into the instrument wherein the cartridge and the instrument are separable.

In the following possible further features and advantages of the device according to the first exemplary embodiment will be explained in detail.

In other words, by inserting the cartridge into the instrument a complete dry propagation path for the focused acoustic energy from the source to the sample is generated. All different dry components of the instrument, the cartridge, the full solid coupler and the source are thus connected in a complete dry manner after inserting the cartridge into the instrument. The coupler in general transmits the acoustic energy from one of its end to another. It shall explicitly be noted, that the full solid coupler is arranged at the device in such a way, that it complements or completes the propagation path of the acoustic energy between the source and the cartridge in a dry way. In other words the propagation path comprises before insertion of the full solid coupler a first dry partial propagation path and a third partial propagation path. By inserting the coupler between these two parts, the missing second partial path is supplied. The complete propagation path may for example be formed firstly out of a material attached to a focusing transducer, secondly out of polymer based coupler and thirdly out of a foil between the coupler and the cartridge. Thus a complete dry coupling between the source and the cartridge is achieved. Thus the full solid coupler does not have to form the whole propagation path by itself, but if it is desired, an exemplary embodiment of the invention may realize this.

Therefore, the use of water or hydrogel or any gel containing liquid substances is avoided. Thus after a completion of an irradiation of the sample with the acoustic energy a clear distinction between a possibly leaking cartridge containing liquid matter and the coupling media can be made. In other words, situations with a high contamination risk due to the leakage of a cartridge may be recognized by a user of the device more clearly and even faster.

As the instrument and the cartridge are totally different components that are physically separated or at least separable the volume of the sample to be treated can be chosen by selecting different cartridges. Furthermore the chamber of the cartridge may not be totally filled with the sample and thus having an additional air layer within the chamber above the sample. This may arise in several technical advantages compared to so-called flow through systems. An exemplary advantage of an air layer above the sample is that with HiFu vigorous mixing could be introduced, allowing treatment of sample volumes much larger than the focal zone volume. For example by creating a fountain of the sample liquid by means of HiFu irradiation a mixing mechanism via circulation of the sample liquid that is imminent in the fountain cycle can be supplied. Thereby the focal zone in which the HiFu energy creates the fountain may be quite small compared to the sample volume, but nevertheless a mixing process is initiated by HiFu via the fountain. Thus the need to irradiate the whole sample volume that is to be mixed may be avoided by this exemplary embodiment of the invention. In other words a large sample may be treated by a relatively small device.

Additionally HiFu could create a fountain, which may be used to create cavitation at relative low (reduced) powers. The cavitation nuclei may be introduced in the sample by the fountain droplets returning to the liquid which may reduce the power-threshold compared with homogenous cavity in water with an order of magnitude. In other words by creating a fountain out of the sample (e.g. when the sample is a liquid)

the minimum power for the transducer and thus the minimum acoustic energy to be emitted from the source can be reduced. This may lead to advantages described in the context of the present invention.

In other words the fountain could in addition to cause a mixing in the sample and a reduction of cavitation power threshold be used for cooling the sample, as the fountain creates much larger contact surface of the sample with the surrounding air within the cartridge.

The physical separation of the cartridge and the instrument may lead to a non-integrated system which means that the source, the coupler and the cartridge may be chosen and applied for a measurement independently from each other. In other words when the interface between the three constituting parts of the system (source, coupler and cartridge) is defined an independent choice of those three constituting parts may be made as long as the choice fits with the interface.

Because of the fact, that the size of the cartridge and the chamber are independent from the size and shape of the source and of the coupler an enlargement of the cartridge volume is possible without having the need to change the acoustic characteristics of the device. A disadvantage of flow through systems compared to this embodiment of the invention may be that an enlargement of the chamber is possible without having to increase also the transducer.

Additionally it may be relied on focusing onto a focal zone and avoiding a dependency of an interaction of the acoustic energy with a wall of the chamber. In other words the walls of the chamber are not used as a transducer. In contrast to that known systems have to take into account that resonance frequencies of chamber walls are functions of geometry and material properties. These systems have to match that with the source frequency. As it is not relied on interactions of the acoustic field and the walls in such a described way, an enlargement of the chamber may be done independently from the transducer choice.

As the cartridge is physically separable from the instrument the cartridge may be a disposable, consumable and removable cartridge which may lead to a cheap system for analyzing the sample with focused acoustic energy. After a treatment of the sample the cartridge may be discarded without having the need to discard the source or the coupler. Thus a plurality of measurements provided by one single instrument and one solid coupler and one source for a variety of different cartridges with different samples is a possible way using dry coupling.

The device may further comprise a lens for focusing the generated acoustic energy onto the sample.

Furthermore the irradiation of the sample by focused acoustic energy causes a treatment of the sample.

The source or transducer could be a flat or curved piezo transducer operating between kHz up to MHz frequencies. The diameter of the transducer may be for example between 5 mm and 35 millimeters (mm) to fit with the volume range, for example between 0.2 milliliters (mL) and 10 mL, one would like to process in the cartridge. The focal length of the transducers may vary from 5 mm to 80 mm. Transducer electric input power may vary from 2 watts (W) to 100 W. According to this exemplary embodiment of the invention the treatment of samples is possible with lower powers compared to related known technology. Thus heating due to acoustic energy absorption of circumjacent matter, especially of the matter between the source and the sample is avoided, enabling the introduction of dry coupling.

The transducer may operate in a continuous mode or in a burst mode. Applied signal to transducer could have different and varying forms: e.g. sinusoidal, block, triangular, or any combination thereof. Frequency may be additionally adjusted to compensate for frequency shift to heating or to switch focal length.

The cartridge may have one of the following characteristics: disposable, consumable, removable, may contain one chamber or a lot of chambers, may contain one sample or a lot of samples, industrial applicable. The cartridge material is not limited to but may further for example be polyethylene (PE), polypropylene (PP), polyethylene terephthalate (PET); polymethylpentene (PMP), Polymethylmethacrylate (PMMA), polycarbonate (PC) and polystyrene (PS).

In addition to that the cartridge is also a physically independent device from the coupler. Thus the cartridge is different and separable from the instrument and also from the coupler. This exemplary embodiment of the invention does not exclude, that the coupler is placed or fixed onto the cartridge or the instrument, but contains this possibility.

One main advantage is that all desired and needed processing of the sample may be done in one single chamber of the cartridge. Furthermore the whole processing by the applied acoustic energy may be done according to the sample-in result-out principle with all necessary actuation coming from one single source of the device. By means of the focused acoustic energy the sample may be treated with a lot of different functionalities like sample pretreatment and lysis in one single chamber being a process chamber. Especially HiFu may be used for these processes.

To achieve a high intensity of the acoustic energy at the receiving position (chamber in cartridge and thus at the sample) it is preferred that the focus quality of the source or transducer and/or lens is sufficient, that the acoustic attenuation of the materials in the propagation path of the acoustic energy is sufficiently low which means a low impedance and/or a low thickness, and that reflection at the material interfaces in the propagation path of the acoustic energy is sufficiently low which means for the dry coupler that the thickness and roughness of the two contacting layers should be sufficiently small. This exemplary embodiment of the invention meets these requirements.

Power may be supplied to the source from the instrument via e.g. leads or brushes. The full solid coupler may comprise different pieces, parts or segments.

Furthermore the dry coupling may induce, that on the microscale the contact between for example the source and the coupler (first layer) and/or the coupler and the cartridge (second layer) may approach direct contact condition, in other words as close as possible in order to achieve efficient dry coupling. Thus the surfaces of the two layers may be on the microscale or nanoscale as conformal as possible to minimize or eliminate air-pockets between the two layers in dry contact.

In other words to minimize or eliminate air pockets the following requirements may be met by the device: The surface roughness may be sufficiently low of the source, the coupler, the cartridge, the full solid coupler and an interface medium. Also the used materials may be sufficiently "flexible" to achieve conformality. Thereby a conformality order may be considered liquids>hydro gels>solid gels>rubbers> (elastic) foils>thermoplastic polymer>thermo harders, metals, ceramics and other solid materials.

The acoustic energy or acoustic radiation may propagate through a first part of the path unfocused and may later be focused within a second part of the path to propagate focused through a third part of the path till the sample. Previous or subsequent focusing is also possible.

The required power for creating a cavitation process in the sample may be reduced by this exemplary embodiment of the invention, as additional nucleation sites may be introduced in the chamber (e.g. an element with an appropriate high surface roughness e.g. a rod) or a fountain may be induced. Droplets falling back from the fountain into the sample may reduce this power threshold. As the present construction enables both possibilities low power HiFu may be used for preparing and treating the sample.

As the required power may be decreased by the present invention, additional refraction, being generated at high intensities, may be avoided.

According to another exemplary embodiment of the invention the focused acoustic energy is high intensity focused ultrasound (HiFu).

Thereby the source frequencies may be in the range of 0.2 MHz to 10 MHz, with amplitudes chosen to be sufficient efficient to create high pressure shock-waves and/or cavitation in the focal zone. Focal zone dimensions may be dependent on the source transducer type. Exemplary length-scales for the indicated frequency range are (sub) millimeters. Furthermore flat or curved piezo transducer may be used operating between 0.2 MHz and 10 MHz, or between 0.75 MHz and 3 MHz, or between 1 MHz and 2 MHz. The diameter of the transducer may be for example between 5 mm and 35 mm to fit with the volume range (0.2 mL-10 mL) one would like to process in the cartridge. The focal length of the transducers may vary from 5 mm to 80 mm. Transducer electric input power may vary from 0.5 W to 100 W.

In other words, this exemplary embodiment of the invention may be used as a HiFu molecular device for treating and/or analyzing molecular samples. Thereby no liquid matter must be used for coupling the acoustic energy from the source to the sample. Thus liquid contamination risks may be reduced and by using disposable or consumable cartridges an uncomplicated, cheap and fast way of measuring characteristics of the sample plus preparing the sample with the device and thus with HiFu may be provided.

Due to the relatively short wavelength of HiFu compared to ultrasound, an enhanced focusing onto a smaller region is possible. This leads to a miniaturization advantage.

In addition to that various different focal region shapes may be used for treating the sample by the HiFu.

As HiFu enables a user to treat a sample e.g. with functionalities like mixing with a reagent, circulation, release of a cell, pathogen and matrix from a swab, release of a cell, pathogen and matrix from a brush, liquefaction, incubation of the sample with a reagent at room temperature or elevated temperature, shaking, mixing; stirring, extraction, NA extraction, flow generation, sample homogenation, separating by centrifuging, and any combination thereof, lysis, lysis of microorganisms, incubation of the sample with a reagent at room or elevated temperature, and any combination thereof a huge variety applications for the device is created.

Furthermore known systems may be limited dictated by physics because real miniaturization of the ultrasound transmitter may not be possible; known systems may thus be limited to about 100 mm. This embodiment of the invention may be miniaturized smaller than 100 mm.

Further on another disadvantage of known systems may be that the resonance frequency of the ultrasound chamber is design and material dependent and should be matched with the chosen ultrasound transmitter frequency. Manufacturing tolerances may have to include this dependency. In contrary to that, any resonance frequency of the device may not have been taken into account, as described above.

Furthermore other instruments using acoustic energy may be limited to a small volume chamber as according to basic physical laws of mechanics an increasing in dimensions means a reduction of the resonance frequency of the chamber or the system. Parallel existing requirements of the ultrasound frequency originating in the specifications of the sample may thus make it useless to increase the size of the chamber. This may limit the spectra of the applications of such a known instrument.

In contrary to that, a non integrated system is presented, in which the cartridge is physically independent i.e. separated from the source and the coupler, as described above. It may be that no resonance frequency of the chamber has to be taken into account, when selecting the desired size of the cartridge or the chamber. This is an important advantage above the known technology.

Furthermore this exemplary embodiment is enabled to avoid, if necessary, a flow-through technique, which may complicate the combination with incubation at elevated temperature. In addition these flow-through technologies may have the need to provide some kind of beads to the chamber. But in the case a flow through may be desired, the present idea is able to provide for that.

In other words this exemplary embodiment of the invention distinguishes from technologies using ultrasound impacting the wall of the chamber. In these known systems the resonance frequency is dependent from geometry and/or the material of the device.

Furthermore in contrast to flow-through systems which use homogenous cavitation, the power can be reduced in this exemplary embodiment, as this exemplary embodiment of the invention may supply for an air layer in the chamber, which makes it possible to introduce nucleation sites or to produce a fountain as described above. By means of additional nucleation sites like a rod that is introduced in the chamber or by means of the described fountain, the power threshold to initiate cavitation may be reduced. Furthermore it may be provided for an incubation possibility of the sample although not all of the sample fluid has to be in the focal zone.

This may enable the user to use smaller transducers and less power which enables the introduction of the full solid coupler or dry coupling. Furthermore the combination of incubation may be facilitated.

In addition to that this exemplary embodiment of the invention is able to use additional different functions, e.g. elution of swabs in a process chamber. As HiFu is used with dry coupling, it allows detection of cartridge leakage and therefore contamination could be detected in an early stage.

According to yet another embodiment of the present invention a source is one of part of the instrument or part of the cartridge.

In a first example of this embodiment the source may be implemented in the instrument of the device. Thus a plurality of cartridges may be irradiated one after another by one and the same acoustic energy source. Thus measurement results of different cartridges may be more comparable and reliable as deviations originating from different sources can be excluded.

In a second example of this embodiment of the invention the source is part of the cartridge. For example, a cartridge may be provided with a source and a full solid coupler being situated between the source and the cartridge. For example, they may be glued together to one unit. Also other fixation possibilities shall be comprised. By inserting this unit into the instrument the electric connection between the power supply for the source is plugged together. Thus a complete dry coupling is generated in this embodiment of the invention.

By means of the integration of the source into the cartridge a pre-selection or pre-adaption of the specific source for certain measurement intentions is possible. Thus in combination with the instrument different types of cartridges with specifically selected sources for these cartridges and for specific measurements may be used with one single instrument. This means an increase operation field of the instrument. In addition to that the cartridges and the sources being attached to the cartridges may be disposable and thus may provide a cheap and uncomplicated solution for treating different samples in different cartridges with different sources attached by one single instrument.

According to another exemplary embodiment of the invention, the instrument and the cartridge are arranged in combination in such a way that by inserting the cartridge into the instrument the propagation path for transmitting the acoustic energy from the source to the sample is formed wherein the propagation path comprises only of non-fluidic matter.

In other words, the interaction of the cartridge and the instrument during the insertion process yields to the complete dry coupling propagation path. Therefore, the corresponding surfaces of the instrument and the cartridge are brought together during an insertion process and they may be shaped in a for example form-closed way or in a force-fit way. In addition to this shape fitting of the contour of the instrument and the cartridge extra means for applying a pressure between these elements and the additional coupler may be provided. In other words, only solid materials or gaseous materials, like air pockets, are present in the propagation path of the acoustic energy.

According to another exemplary embodiment of the invention, the full solid coupler is formed out of the material selected from the group comprising solid gel, rubber, elastic foil, polymer based material, thermoplastic polymers, polymer having a low acoustic attenuation characteristic, metal, semiconductor, ceramic, polypropylene, aluminum, and a stack of these materials.

It shall explicitly be noted, that the full solid coupler may be formed out of a polymer based material.

The used materials may obey elastic characteristics that allow a conformable adaption of the coupler to the shape of a component of the device for example of the cartridge or of the source. Thereby the material of the full solid coupler may be chosen in such a way, that air pockets at any interface within the propagation path are minimized or avoided to achieve efficient dry coupling. Furthermore the full solid coupler may also contain the above mentioned materials as partial components and other not mentioned materials may be contained in the full solid coupler.

Calculations have shown that the stack could increase the amount of energy which could be transferred to the receiving position, but at the expense of a more complicated coupler. In other words impedance matching may be used. Thus the full solid coupler may comprise several components, that together yield to a complete and efficient dry coupling of the acoustic energy from the source to the sample.

According to another exemplary embodiment of the invention, the cartridge comprises an acoustic window wherein the acoustic window is made of a flexible foil and wherein the full solid coupler is physically contacted with the acoustic window by inserting the cartridge into the instrument.

In order to achieve a high intensity of the focused acoustic energy at the receiving position (chamber in the cartridge where the sample is positioned) it may be essential that the attenuation of the materials in the transport path of the HiFu is sufficiently low. Furthermore air pockets shall be minimized or eliminated by using surface roughness's that are sufficiently low. Also materials that are sufficiently flexible to achieve conformity may be used. These requirements may be met by the acoustic window that is made out of a flexible material like a plastic foil. Thereby the plastic foil may adapt its shape during an insertion of the cartridge into the instrument to the shape of the contact surface of the cartridge or the shape of the full solid coupler.

The acoustic window of the cartridge may be sufficiently large that the cross section of the HiFu cone at the chosen acoustic window distance fits completely in the window. The acoustic window could be flat or curved. The acoustic window is of made of a thin layer of a low attenuation polymer, e.g. PP, PMP. It is also important that the remaining part of walls of the lysis chamber below the fluid level may be sufficiently thin to reduce acoustic losses and to limit heating of the chamber housing.

According to another exemplary embodiment a contact pressure between the full solid coupler and the cartridge is applied, wherein the contact pressure is generated by at least one method from the group comprising applying over pressure in the chamber of the cartridge, applying local under pressure outside of the cartridge, and pressing the cartridge and the full solid coupler against each other by means of a force.

The contact pressure between the solid coupler and the cartridge surface is applied in a sufficient way to get rid of air or air pockets at the interface or at any intermediate layer in the propagation path of the acoustic energy. Pressing e.g. a convex shaped solid coupler against a flat cartridge, with the cartridge material being sufficiently flexible to become conformal to the shape of the solid coupler may be possible solution. In addition to that the coupler may also have such a flexibility.

Another exemplary embodiment may be a dry interface solution comprising a smooth spherical or conical shaped HiFu transducer and a flexible cartridge foil.

Thereby the contact pressure yields to a force that presses a least the three components source, coupler and cartridge together in such a way, that air pockets may be minimized between some or all intermediate contacting surfaces. Therefore especially smooth and flexible materials may be used for these surfaces.

According to another exemplary embodiment of the invention, the full solid coupler has a first contact surface for contacting the acoustic window and the cartridge has a second contact surface for contacting the acoustic window. Furthermore at least one of the first contact surface, the second contact surface and the acoustic window has a surface roughness value selected from the group comprising smaller than 0.5 micrometers ($\mu m$), smaller than 1 $\mu m$, and smaller than 2 $\mu m$.

Due to this embodiment of the invention air pockets and thus transmission losses in the propagating acoustic energy may be minimized or eliminated.

An interface medium between the instrument and cartridge to enable acoustic energy transport across dry interface may be made of a low attenuation material like rubber (e.g. RT 615), (elastic) foil (e.g. PP, PP based Thermoplastic Elastomer, PMP), or thermoplastic polymer (e.g. PP). The interface layer could be part of the instrument or of the cartridge. For example the cartridge bottom layer contacting the coupler could also be at the same time the interface medium.

According to another exemplary embodiment of the invention, the propagation path has a gradient of acoustic impedance, wherein the gradient is monotonously decreasing in a direction from the source to the sample.

This embodiment may lead to further reduction of acoustic energy losses, as a coupling from one component to another component in the propagation path may be improved due to the gradient of the acoustic impedance. By applying such an acoustic impedance profile within the propagation path reflection and absorption of the focused acoustic energy may be reduced. This may lead to a better yield or spoil of a given power.

The acoustic impedance of the materials used within the propagation path of the acoustic energy is going from relative high on the side of the source to relative low at the sample/cartridge site. In addition to that principle laws of acoustics may be used to optimize the choices of dimensions and material of the device and its components.

According to another exemplary embodiment of the invention, the full solid coupler is selected from the group comprising a coupler being a physically separate component placed between the source and the cartridge, a coupler being part of the source, a coupler being part of the cartridge and any combination thereof.

For example, a configuration with the source being a piezo transducer combined with a metal lens on top that has a polymer coupler on top of the metal lens is possible. Also a curved source working simultaneously as a lens may be provided with a polymer coupler on top of that curved source. The coupler may physically be bonded to the source or the cartridge but it can also be hold on top of one of these components by external pressure applied to these components. Referring now to the following FIGS. 10 to 14 a large variety of combinations of arranging and fixing the coupler between the source and the cartridge are possible. Placing the coupler on the source, on the cartridge, on a lens, on a second additional coupler and on an acoustic window with different fixation possibilities like pressing together, gluing together, depositing a coupler on a component, and any combination thereof are comprised within this embodiment of the invention.

According to another exemplary embodiment of the invention, a lens for focusing the generated acoustic energy onto the sample is further comprised. Thereby the lens is selected from the group comprising a lens being a physically separate component placed between the source and the cartridge, a lens being part of the source, a source with a focusing shape being the lens, an array of sources that yield to a focus acoustic energy, a lens being part of the cartridge, a lens made out of a polymer, having a low acoustic attenuation characteristic, a metal lens, a ceramic lens, a polypropylene lens, an aluminum lens, a hybrid lens and any combination thereof.

Lens may be made of a low attenuation polymer, metal or ceramic. For environmental reasons the lens may be integrated in the consumable and made of a polymer, e.g. PP.

As a first characteristic of the lens the lens is able to focus the generated acoustic energy onto the sample. In order to reduce the transmission losses the lens may be attached to the source. For example a metal lens may be fixed onto a piezo transducer yielding to the emission of a focused acoustic field. Furthermore an array of a plurality of sources may be spatially placed in such a way and electronically driven in such a way that the superposition of all the singular acoustic fields yields a focused acoustic field. Furthermore it is possible that the lens is part of the cartridge for example being fixed to the bottom of the cartridge. In addition to that this example may further comprise a source being part of the cartridge.

In order to create multi-focality also a hybrid lens may be used in this exemplary embodiment of the invention. Thereby the lens has at least two different emitting zones which means, that the different emitting zones of the lens deviate from each other by at least one of the following components shape, surface roughness, material, and any combination thereof. To shortly summarize the function of a hybrid lens it has to be said that an incoming homogeneous acoustic field will be transferred by the hybrid lens into a non-homogenous acoustic field having for example two different focal regions.

According to another exemplary embodiment of the invention, in the one single chamber of the cartridge pretreatment and lysis are applied to the sample by means of the focused acoustic energy. Thereby pretreatment is a method selected from the group comprising mixing with a reagent, circulation, release of a cell, pathogen and matrix from a swap, release of a cell, pathogen and matrix from a brush, liquefaction, incubation of the sample with a reagent and/or enzyme at room temperature or elevated temperature, shaking, mixing, stirring, extraction, NA extraction, flow generation, sample homogenation, separating by centrifuging and any combination thereof. Furthermore lysis is a method selected from the group comprising mixing with a reagent, mixing with a reagent different to the reagent applied during pretreatment, circulation, lysis of microorganisms, incubation of the sample with a reagent at room or elevated temperature or a temperature different from the temperature applied during pretreatment and any combination thereof.

It shall explicitly be noted that this combination of pretreatment and lysis in one single chamber by means of the focused acoustic energy originating from only one single source may be applied without providing a dry coupling. No full solid coupler or a propagation path out of completely dry media is necessary.

Accordingly, a second aspect of the present invention is directed to the application of pretreatment and lysis to the sample by means of focused acoustic energy in the one single chamber of the cartridge, i.e. in particular in the same chamber. An exemplary embodiment of this aspect of the present invention provides a device for irradiating a sample with focused acoustic energy to treat the sample, the device comprising an instrument, a cartridge, and a source for generating the acoustic energy. The cartridge has a chamber for receiving the sample. The instrument and the cartridge are adapted for inserting the cartridge into the instrument. The cartridge and the instrument are separable. The device is designed such that pretreatment and lysis are applicable to the sample in the chamber of the cartridge by means of the focused acoustic energy.

In addition to that an exemplary embodiment of this second aspect of the present invention further relates to a corresponding instrument for irradiating a sample with focused acoustic energy to treat the sample, the instrument comprising a source for generating the acoustic energy. The instrument is adapted to receive a cartridge being separable from the instrument, the cartridge providing a chamber for receiving the sample. The instrument is designed such that, when the cartridge is being inserted in the instrument, pretreatment and lysis are applicable to the sample in the chamber of the cartridge by means of the focused acoustic energy.

Correspondingly, a cartridge is provided in another exemplary embodiment which cartridge for an instrument for irradiating a sample with focused acoustic energy generated by a source to treat the sample comprises a chamber for receiving the sample. The cartridge is adapted for being inserted into an instrument and being separable from the instrument. The cartridge is designed such that when being inserted into the instrument pretreatment and lysis are applicable to the sample in the chamber by means of the focused acoustic energy.

In addition to that exemplary embodiments of this aspect of the invention further relate to a corresponding method for pre-treating and lysing a sample in one single chamber by means of focused acoustic energy like for example HiFu originating from one single source, preferably by such device, and a computer program element characterized by being adapted when being used to control a device for pre-treating and lysing a sample to cause the device for performing the steps of this corresponding method.

These exemplary embodiments may for example combine pretreatment and lysis in a single chamber by using single focus HiFu, but also the use of multi focus HiFu is possible. But also any combination with incubation is possible.

In other words, manual steps for doing sample pretreatment can be avoided by an exemplary embodiment of the device, the corresponding instrument and cartridge, the corresponding method and the computer program element. Pretreatment is integrated in the cartridge to increase ease-of-use and to decrease fluidic interfacing with the external world and contamination risk. Furthermore pretreatment and lysis functions are integrated in one single chamber that could be exposed to HiFu and/or heated and/or cooled to reduce complexity, costs and size of the device and the procedure for doing treatment and lysis together. Pretreatment and lysis functions advantageously are processed without the sample leaving the chamber in between, and/or advantageously are processed in a fully automated manner, and/or advantageously are processed sequentially or simultaneously.

This second aspect of the invention may be used for any application requiring pretreatment and/or lysis. Applications may not be limited to healthcare, life science, food industries and veterinary practice. This relates to any embodiment of the invention.

Especially for lysing difficult micro-organisms the state of the art technique of applying thermal lysis has several insufficiencies. In contrary to that this aspect of the present invention uses focused acoustic energy, especially HiFu for solving these problems. By means of such a fully integrated in vitro preparation and detection instrument a system for sample-in result-out tests is provided, especially for nucleic acid (NA), protein or cell detection. Furthermore nucleic acid analysis, protein analysis and cell analysis may be possible by a so called micro total analysis system.

Additionally, existing lysing methods comprise grinding or bead beating which may be avoided here.

In general nucleic acid sample preparation protocols are more complicated than cell or protein preparation protocols. Although this aspect of the invention may be for the major part on nucleic acid sample preparation it is not limited to this.

For this reason a single solution with a high flexibility is needed to accommodate these deviations in needed pretreatment. This aspect of the invention meets these requirements with high degree of flexibility on pretreatment and lysis protocols.

It shall be noted that preferred embodiments of other aspects of the present invention shall be considered as preferred and disclosed embodiments with respect to the present aspect, too, and vice versa.

According to another exemplary embodiment of the invention, the device is adapted in such a way that it generates at least two different focal regions at the sample.

It shall explicitly be noted that this exemplary embodiment of the invention may be applied or implemented without having the need to provide for the complete dry coupling features. In other words, the creation of a multi-focality by the device may also be used in combination with non-solid coupling matter.

Accordingly, a third aspect of the present invention is directed to the generation of two different focal regions at the sample. In an exemplary embodiment of this third aspect of the present invention a device is presented for irradiating a sample with focused acoustic energy to treat the sample comprising an instrument, a cartridge, and a source for generating the acoustic energy. The cartridge has a chamber for receiving the sample. The instrument and the cartridge are adapted for inserting the cartridge into the instrument. The cartridge and the instrument are separable. The device is designed for generating at least two different focal regions of acoustic energy at the sample.

In addition to that an exemplary embodiment of the third aspect of the present invention further relates to a corresponding instrument for irradiating a sample with focused acoustic energy to treat the sample, the instrument comprising a source for generating the acoustic energy. The instrument is adapted to receive a cartridge being separable from the instrument and providing a chamber for receiving the sample. The instrument is designed for generating at least two different focal regions of acoustic energy at the sample when the cartridge is inserted in the instrument.

Correspondingly, a cartridge is provided in another exemplary embodiment which cartridge for an instrument for irradiating a sample with focused acoustic energy generated by a source to treat the sample comprises a chamber for receiving the sample. The cartridge is adapted for being inserted into an instrument and being separable from the instrument. The cartridge is designed for allowing generating at least two different focal regions of acoustic energy at the sample when being inserted in the instrument.

Furthermore it shall explicitly be noted that a corresponding method for generating at least two different focal regions at the sample by the device and a corresponding computer program element for controlling a device generating a multi-focality to the sample is comprised within this embodiment. Thereby the computer program element may be characterized by being adapted when in use on a device for creating a multi-focality to the sample to cause the device for performing the steps of the corresponding method.

In other words, a treatment protocol using two different focal zones for providing different focus conditions is provided. For example, focus conditions for doing mixing a liquid circulation by means of focused acoustic energy may be different from the requirements for doing lysis with for example microorganisms. This embodiment of the invention meets these requirements.

By providing at least two different focal regions at the sample the device may provide for attractive simple and cheap molecular diagnostic tests. Furthermore complex arrangements of piezo arrays, complicated systems and/or drivers can be avoided by this exemplary embodiment of the invention. Furthermore the integration of several different functionalities (like e.g. mixing, circulating, and lysing) into one chamber that are processed by the two different focal regions a miniaturization of the molecular diagnostic device is possible.

In other words the molecular diagnostic device is a multi-focality HiFu molecular diagnostic device for applying different focal regions to the sample. This can be used for generating and combining different treatment functionalities. For example point-like focused HiFu may be optimal for doing lysis and zone-like focused HiFu may be optimal for mixing and/or circulating. Thereby point like means a comparatively small focal region, and a zone-like focus means a comparatively large focal region. Different focal regions may also differ in shape and in size. These different focal requirements are met by this exemplary embodiment of the invention.

Furthermore lysis by means of HiFu requires high acoustic pressures. High pressures are achieved by good quality focusing which is achieved by this exemplary embodiment of the invention by means of a first highly focused part of the generated acoustic energy. In contrary to that to release particles or cells from swabs, to release and homogenize feces from a carrier, e.g. swabs, brush, to homogenize liquid present in the chamber with reagents added to the chamber mixing and circulation may be required in one single chamber of the cartridge. Thus a second part of the generated acoustic energy is focused to a comparatively large, zone-like second focal region at the sample. Thus two different treatment functionalities may be applied to the sample during the same time, in one single chamber and without any manual intervention of a user.

According to another exemplary embodiment of the invention, the at least two different focal regions are generated by means of an element selected from the group comprising a plurality of sources, a single source and a hybrid lens, one single source with different roughness zones and one single source being excited differently at different positions of the source, and any combination thereof. Such element may be embodied as an element external to the cartridge, or an element belonging to the cartridge, or as an element integrated into the cartridge.

A plurality of sources comprises at least two single sources, as well as an array of sources being electronically controlled in such a way that the superposition field of all the sources yields to a total field having at least two focal regions. Furthermore the hybrid lens may consist of a moderately focusing material and a highly focusing material. These materials may be positioned at different parts of the lens yielding to multi-focality. For example a concave shaped hybrid lens may be attached to a flat source like a transducer. But also a curved transducer with a curved hybrid lens made out of a moderately focusing material and a highly focusing material is possible. In order to find an optimized distribution of these two different materials acoustic modeling may be performed on different configurations. For example, the lens may be formed out of polypropylene. Furthermore lens radius may vary due to the application of the device. In order to create a multi-focality at the receiving position where the sample is located, the source may also be provided with different roughness zones, which means that the surface of the source obeys different surface roughness values.

The different emitting zones, more detailed the respective surfaces of these zones, may have different roughness properties. These different roughness properties yield to different acoustic irradiating characteristics of the zones, which leads to at least two different focal zones. Thereby the source or transducer itself may have these zones. But also an additional component may be added on top of the transducer, wherein the component obeys these different surface roughness characteristics. In other words the gist of this possibility is that the surface of the transducer is segmented in a smooth and rough area delivering respectively highly and moderately focused acoustic energy, especially HiFu, to the sample.

It shall be noted that preferred embodiments of other aspects of the present invention shall be considered as preferred and disclosed embodiments with respect to the present aspect, too, and vice versa.

According to another exemplary embodiment of the invention, the focused acoustic energy is used for reducing the viscosity of the sample.

It shall explicitly be noted that this embodiment of the invention does not necessarily need to contain all the dry coupling features. In particular no full solid coupler or a completely dry propagation path is necessary.

Accordingly, a fourth aspect of the present invention is directed to using the focused energy for reducing the viscosity of the sample. In an exemplary embodiment of this fourth aspect of the present invention a device is provided for irradiating a sample with focused acoustic energy to treat the sample comprising an instrument, a cartridge, and a source for generating the acoustic energy. The cartridge has a chamber for receiving the sample. The instrument and the cartridge are adapted for inserting the cartridge into the instrument. The cartridge and the instrument are separable. The device is designed for using the focused acoustic energy for reducing the viscosity of the sample.

In addition to that an exemplary embodiment of the fourth aspect of the present invention further relates to a corresponding instrument for irradiating a sample with focused acoustic energy to treat the sample, the instrument comprising a source for generating the acoustic energy. The instrument is adapted to receive a cartridge being separable from the instrument and providing a chamber for receiving the sample. The instrument is designed for using the focused acoustic energy for reducing the viscosity of the sample when the cartridge is inserted into the instrument.

Correspondingly, a cartridge is provided in another exemplary embodiment which cartridge for an instrument for irradiating a sample with focused acoustic energy generated by a source to treat the sample comprises a chamber for receiving the sample. The cartridge is adapted for being inserted into an instrument and being separable from the instrument. The cartridge is designed for allowing reducing the viscosity of the sample by means of focused acoustic energy applied to the sample when being inserted into the instrument.

In addition to that an exemplary embodiment comprises a corresponding method for reducing the viscosity of the sample, preferably by such device, and a corresponding computer program element. Thereby the computer program element is characterized by being adapted when in use on a device for reducing the viscosity of the sample by means of irradiating the sample with focusing acoustic energy to cause the device for performing the steps of the corresponding method.

In order to reduce the viscosity of a sample like for example BAL, sputum, blood, feces, or any other sample present on a swab this embodiment of the invention suggests to use focused acoustic energy for example HiFu to cause this reduction. This method may be implemented in a complete sample-in result-out solution in which a subsequent pretreatment and lysis of the sample may be possible in the one chamber of the cartridge. Thus by means of only one single source a complete process of viscosity reduction, further pretreatment and lysis is possible.

For example, a source having the following characteristics may be used for the reduction of the sample viscosity. 3.0 MHz transducer with a diameter of 25 mm a focal length of 22 mm. Furthermore the bottom of the cartridge may be set at 15 mm distance of the transducer. Exemplary power of 5 W may be applied to the sample for approximately 300 s. By means of such a HiFu application the sample may be more homogeneous after such a HiFu exposure and the viscosity may drop from the original viscosity to for example a water-like viscosity. Thus it can be concluded that HiFu forces combine the ability to reduce the molecular weight of the macromolecules and as a result the viscosity and the ability to circulate and mix a sample in a process chamber.

It shall explicitly be noted that this exemplary embodiment of the invention may be used for any application requiring circulation and/or mixing in the sub-millimeter volume range in a device. The applications may be also in the life sciences, lab-on-the-chip, and mTAS applications.

It shall be noted that preferred embodiments of other aspects of the present invention shall be considered as preferred and disclosed embodiments with respect to the present aspect, too, and vice versa.

According to another exemplary embodiment of the invention, a detection unit for applying measurements on the sample is further comprised. Thereby the irradiation of the sample with the focused acoustic energy leads to a treatment of the sample.

In other words, this exemplary embodiment of the invention provides for a complete sample-in result-out system, where no manual step has to be done by the user. A sample may be inserted into the device and by means of the focused acoustic energy the sample is treated in a desired way. Subsequently or also previously measurements may be applied to the sample by means of the detection unit. Thereby the device is enabled to deliver the measurement results to for example a user interface to the user. For example, functionalities like liquefaction, stirring, mixing, circulation, pretreatment, incubation and lysis may be done before or after any measurement of the detection unit by means of the focused acoustic energy. A fully automated system is thus provided to the user.

It shall further be noted that this exemplary embodiment of the invention may not necessarily contain all dry coupling features. In particular, no full solid and dry coupler or a completely dry propagation path is necessary.

Accordingly, a fifth aspect of the present invention is directed to a detection unit for applying measurements on the sample. In an exemplary embodiment of this fifth aspect of the present invention a device is provided for irradiating a sample with focused acoustic energy to treat the sample comprising an instrument, a cartridge, and a source for generating the acoustic energy. The cartridge has a chamber for receiving the sample. The instrument and the cartridge are adapted for inserting the cartridge into the instrument. The cartridge and the instrument are separable. The device comprises a detection unit for applying measurements on the sample.

In addition to that this exemplary embodiment of the invention further relates to a corresponding instrument for irradiating a sample with focused acoustic energy to treat the sample, the instrument comprising a source for generating the acoustic energy. The instrument is adapted to receive a cartridge being separable from the instrument and providing a chamber for receiving the sample. The instrument comprises a detection unit for applying measurements on the sample when the cartridge is inserted into the instrument.

Correspondingly, a cartridge is provided in another exemplary embodiment which cartridge for an instrument for irradiating a sample with focused acoustic energy generated by a source to treat the sample comprises a chamber for receiving the sample. The cartridge is adapted for being inserted into an instrument and being separable from the instrument. The cartridge is designed such that when being inserted into the instrument a detection unit may apply measurements on the sample.

In addition to that it shall be noted that this exemplary embodiment comprises a corresponding method for applying measurements on the sample by such device and a corresponding computer program element. Thereby the computer program element is characterized by being adapted when in use on such a sample-in result-out system to cause the device for performing the steps of the corresponding method.

This allows in vitro treatment of the sample by means of e.g. HiFu and at the same time in vitro detection which leads to a complete sample-in result-out system.

Especially for a molecular device being a device according to an embodiment of the invention and which device is enabled to extract, purify, amplify and detect nucleic acids it shall be stated the following: Extraction and/or purification of nucleic acids is based on adsorption and/or desorption on a solid surface. Any surface offering sufficient capture area should be regarded as a part of an embodiment of the invention. Common surface capture embodiments are (for example magnetic) particles and membranes. Any capturing material capable of delivering nucleic acids of sufficient quality for multiplication purposes should be regarded as part of an embodiment of the invention. Widely used materials are e.g. silica, magnetized silica, iron-oxide, aminogroup functionalized polystyrene. Also other materials are possible.

The detection unit and thus the detection method of choice may be dependent on the application area like e.g. nucleic acids, protein or cell detection.

For nucleic acid amplification and detection e.g. a large number of isothermal and thermal cycling amplification methods are described. Polymerase chain reaction (PCR) is one of the most used methods. The sample-in result-out system according to this exemplary embodiment of the invention implements such a PCR functionality into the chamber where the sample is also treated by means of HiFu.

PCR is further subdivided in two subcategories namely end-point and real-time PCR (rtPCR). Of these two rtPCR is most widely used (rtPCR amplification is running in parallel with detection). For detection of nucleic acids one may for example use detectable markers such as fluorescent markers which may be incorporated in the amplified nucleic acids during PCR. Other detectable labels or even label-free methods may also be used.

For protein detection, common approaches such as a combination of antibody capture and optical readout, e.g. fluorescence, of magnetic readout may be used.

For cell detection, optical methods as they are widely used to count, analyze cell shape, etc, but (di) electrophoretic and electrical properties could also used to detect/characterize cells.

All the before mentioned detection possibilities of this embodiment of the invention correspond to the detection unit that is used in this embodiment of the invention. Thus the realized sample-in result-out system may incorporate any of these detection or measurement features.

According to another exemplary embodiment of the invention, the detection unit is for applying at least one measurement to the sample selected from the group comprising optical measurements, magnetic measurements, thermal measurements, electrical measurements, chemical measurements, sonic measurements, and any combination thereof.

The device may further comprise at least one of: an extraction unit; a nucleic acid amplification unit; a reagent storage unit; a detection unit a detection unit for applying measurements on the sample wherein the detection unit is for applying at least one measurement to the sample selected from the group comprising optical measurements, magnetic measurements, thermal measurements, electrical measurements, chemical measurements, sonic measurements, and any combination thereof. According to this embodiment the apparatus may comprise, for instance: an extraction unit; an extraction unit and a nucleic acid amplification unit; an extraction unit, a nucleic acid amplification unit, and a detection unit. In each of these options a reagent storage unit may be present in addition to the elements of each option listed in the previous sentence. The extraction unit allows a nucleic acid to be obtained from a sample processed by the apparatus. The nucleic acid amplification unit allows a nucleic acid obtained from the sample to be amplified (using, for instance, PCR).

The reagent storage unit comprises a reagent needed for, for instance, extraction and/or amplification.

In order to have a wide spectrum of measurement possibilities different types of sensors and detectors may be installed within the device. Additionally it may be advantageous to combine the already existing ultrasonic means for actuating or treating the sample with the possibility to do sonic measurements. The detection unit may be also part of the cartridge. In other words optical readout, but also other detection labels e.g. magnetic, electrical, electro-magnetic especially radio-frequency applied techniques but also labellers methods are possible.

According to another exemplary embodiment of the invention, the device further comprises a processor for coordinating a treatment protocol, a data processor, a display and a user interface.

It shall be noted that preferred embodiments of other aspects of the present invention shall be considered as preferred and disclosed embodiments with respect to the present aspect, too, and vice versa.

According to another exemplary embodiment of the invention the full solid coupler is made out of a polymer based material; and wherein the polymer based material has a glass transition temperature $T_g$ selected from the group comprising: $T_g \geq -30°$ C.; $T_g \geq -10°$ C., $T_g \geq -5°$ C.; $T_g \geq 20°$ C.; $T_g \geq 40°$ C.; $T_g \geq 60°$ C.; $T_g \geq 80°$ C.; $T_g \geq 100°$ C.; $T_g \geq 120°$ C.; $T_g \geq 130°$ C.; $T_g \geq 140°$ C.; $T_g \geq 150°$ C.; and $T_g \geq 160°$ C.

It shall be noted, that the relevance of the glass transition temperature of the material of the full solid coupler gets more important the higher the intensity of the HIFU is. For low intensity, for example when the input power P of the transducer is smaller than 3 Watt the value of $T_g$ may not be that relevant. This may be seen in FIG. 22. Medium intensity, P being e.g. between 3 and 6 Watt, self enforced attenuation as described above and hereinafter may play a more serious role which may require a polymer with a sufficiently high $T_g$. At high intensities above e.g. 6 Watt the relevance of the choice of the polymer based on his $T_g$ value even gets more important.

It may be necessary that at high intensity HiFu applications at room temperature the $T_g$ may have to be above room temperature (approximately 50° C.).

It has been found that materials with relative high glass transition temperature $T_g$ keep contrary to lower $T_g$ materials during operation of the device and thus during the acoustic energy transmission their low attenuation characteristics. Thus an application of these low-attenuation high-$T_g$ materials as full solid couplers enables very efficient transmission of ultrasound intensities relevant for e.g. treatment of samples, e.g. lysis of cells. Especially for HIFU applications as defined above this is an advantageous effect realized by the invention. In other words by using these materials a reduced power provided to the source may be necessary to realize a certain HIFU power in the focal region. Thus treatment and/or pre-treatment functionalities may be realized with a reduced power value. This may save energy and costs. In other words the effect of self-enforced attenuation of the coupling material may be avoided by the invention. The attenuation per meter of the propagation path may thus be reduced.

In order to provide for a better understanding of this exemplary embodiment of the invention the following description of the physical processes shall be noted:

Intrinsic to attenuation is that the coupler material temperature may start increasing. Further the attenuation of acoustic energy may also increase in parallel. This exemplary embodiment of the invention now provides for materials that have the advantage to keep a relatively low attenuation even when their temperature starts increasing during e.g. HIFU operation in the MHz range.

Examples for such materials may be polypropylene with $T_g$ approximately −18° C., epoxy with $T_g$ approximately 60° C. and silicons with $T_g$ approximately 60° C., approximately 100° C. and approximately 125° C.

It has to be noted that a sufficiently high glass temperature is related to the attenuation at the start of the test, the ultrasound intensity, the thermal conductivity of the setup (transport of heat generated) and the exposure time.

In other words the choice of the polymer with a certain $T_g$ value depends on several parameters like the attenuation value of the polymer at the beginning of the HIFU transmission through the polymer as full solid coupler and thus before any absorption or heat generation has started. Furthermore the applied intensity or the power of the source determines that choice of the polymer. Additionally the thermal conductivity of the surrounding of the coupler is a parameter which influences the choice of a polymer with a sufficiently high $T_g$ value. A high thermal conductivity of the system around the coupler results in slower temperature rise and lower maximum temperature, if HiFu is sufficiently long exposed to reach equilibrium.

Especially for relatively high-intensity ultrasound applications this may be particularly relevant. For example when doing lysis with the HIFU energy within the sample the necessary power may be relatively high. Thus for lysing methods using HIFU this exemplary embodiment may be quite advantageous.

In other words the full solid coupler present in the propagation between the source and the destination being the cartridge has a reduced attenuation of the acoustic energy. In addition to that tuned or matched impedances of the materials transmitting the acoustic energy may be used, to minimize reflection losses when passing material interfaces.

Thus the device provides for a complete dry coupling with the possible following advantages: ease-of-use for the operator and reduction of test turn-around-time, as a consequence other applications run by less-skilled personal could be envisioned.

Polymers are a particular advantage class of materials to be used as couplers, because of the rich variety of materials available, the shape and dimensional design freedom, easy replication and associated relative low costs. This may further be described in detail in FIGS. 21 to 23.

According to another exemplary embodiment of the invention wherein the polymer based material has been cured at a curing temperature $T_c$ selected from the group comprising: $T_c \geq 20°$ C.; $T_c \geq 40°$ C.; $T_c \geq 60°$ C.; $T_c \geq 70°$ C.; $T_c \geq 80°$ C.; $T_c \geq 90°$ C.; $T_c \geq 100°$ C.; $T_c \geq 110°$ C.; $T_c \geq 120°$ C.; $T_c \geq 130°$ C.; $T_c \geq 140°$ C.; $T_c \geq 150°$ C.; $T_c \geq 160°$ C.; $T_c \geq 170°$ C.; and $T_c \geq 180°$ C.

The attenuation of the full solid coupler may further be reduced ceteris paribus when the curing temperature of the polymer based material during polymer fabrication is increased. This may further be described in detail in FIGS. 21 to 23.

It has been found, that during the polymer fabrication, which includes a curing process step, the curing temperature during that curing process step at least partially determines the transition glass temperature of the built polymer material. As described above a sufficiently high $T_g$ value has certain advantages for applications in a HIFU molecular device. Thus by defining the curing temperature to a certain value a desired $T_g$ value may be realized in the polymer. Such a process step may be part of a method according to another exemplary embodiment of the invention.

According to another exemplary embodiment of the invention, a method for irradiating a sample with focused acoustic energy to treat the sample is provided. Thereby the method comprises the following steps: providing for an instrument, providing for a cartridge, providing for a full solid coupler, providing for a source for generating the acoustic energy, and inserting the cartridge into the instrument. Furthermore the cartridge has a chamber for receiving the samples and due to the inserting of the cartridge into the instrument a complete dry coupling of the acoustic energy between the source and the cartridge is provided. The cartridge and the instrument are separable.

According to another embodiment of the invention an instrument for irradiating a sample with focused acoustic energy to treat the sample is presented. The instrument comprises a source for generating the acoustic energy, a full solid coupler, wherein the instrument is adapted to receive a cartridge containing the sample, wherein the full solid coupler provides a complete dry coupling of the acoustic energy between the source and the cartridge, when the cartridge is inserted in the instrument; wherein the cartridge and the instrument are separable and wherein the instrument and the cartridge form a device according to one of the above described embodiments.

This embodiment of the invention may be used with HiFu acoustic energy in order to treat the sample with methods or functionalities like mixing and/or lysing in e.g. one single chamber. Furthermore the instrument may comprise a detector and an excitation source that may both be for doing optical, electrical, magnetic and/or mechanical measurements. Additionally a lens may be comprised in the instrument.

In other words the dry coupling may be realized by the full solid coupler that is part of the instrument. Before the presence of the cartridge a complete dry propagation path from the source through the full soil coupler is realized. By inserting the cartridge into the instrument the whole dry propagation path between the source and the sample is completed and the acoustic energy may be transferred to the sample in order to treat the sample.

According to another embodiment of the invention cartridge for an instrument for irradiating a sample with focused acoustic energy to treat the sample is presented, the cartridge comprising a chamber for receiving the sample, a full solid coupler, wherein the cartridge is adapted for being inserted in the instrument. Furthermore the full solid coupler provides a complete dry coupling of the acoustic energy between the source and the cartridge when the cartridge is inserted in the instrument, wherein the cartridge and the instrument are separable and wherein the instrument and the cartridge form a device according to one of the above described embodiments.

The full solid coupler may be permanently fixed to the cartridge. But other solutions are possible. The source may for example be part of the instrument. By inserting the cartridge into the instrument the full solid propagation path between the source and the sample is established.

Furthermore the source may be comprised by the cartridge. Thus by inserting the cartridge into the instrument electrical leads from the instrument are contacted with the source, in order provide the source with electrical energy.

For the two before mentioned embodiments it shall explicitly be noted, that the full solid coupler is arranged at the instrument or at the cartridge in such a way, that the full solid coupler does not have to form the whole propagation path by itself and other additional dry coupling elements may be present. Nevertheless if it is desired an exemplary embodiment of the invention may realize this.

It shall further be noted that a computing unit may be part of the instrument. It may be a separate unit in communication with the instrument, or computing tasks may be distributed over computer unit and instrument.

It shall further be noted that all computer program elements mentioned above as exemplary embodiments of the invention might be stored on a computing unit, which might also be part of an embodiment of the present invention. This computing unit may be adapted to perform or induce the performing of the steps of the method described above. Moreover, it may be adapted to operate the components of the above-described device. The computing unit can be adapted to operate automatically and/or to execute the orders of a user. Furthermore the computing unit can request the selection from a user to process the input from the user.

The embodiments concerning computer program elements cover both a computer program, that right from the beginning uses the computer program element and a computer program that by an update turns an existing program into a program that uses the invention.

According to a further embodiment of the present invention, a computer-readable medium is presented wherein the computer-readable medium has a computer program element stored on it which computer program element is described by the preceding or following sections.

It may be seen as a gist of the invention that a consumable cartridge being separable from the instrument generates a complete dry coupling propagation path for focused acoustic energy when the cartridge is inserted into the instrument. Thereby the dry coupling reaches from the source generating the acoustic energy to the sample.

It has to be noted that some of the embodiments of the invention are described with reference to different subject-matters. In particular, some embodiments are described with reference to methods whereas other embodiments are described with reference to apparatuses. However, a person skilled in the art will gather from the above and the following description that unless other notified in addition to any combination or features belonging to one type of subject-matter also any combination between features relating to different subject-matters is considered to be disclosed within this application.

The aspects defined above and further aspects, features and advantages of the present invention can also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

FIG. 15 shows a schematic image of electronic components being used for a device according to an exemplary embodiment of the present invention.

FIG. 16 shows a treatment protocol that is processed by a device according to an exemplary embodiment of the present invention.

DETAILED DESCRIPTION OF THE EMBODIMENTS

Figure 1:
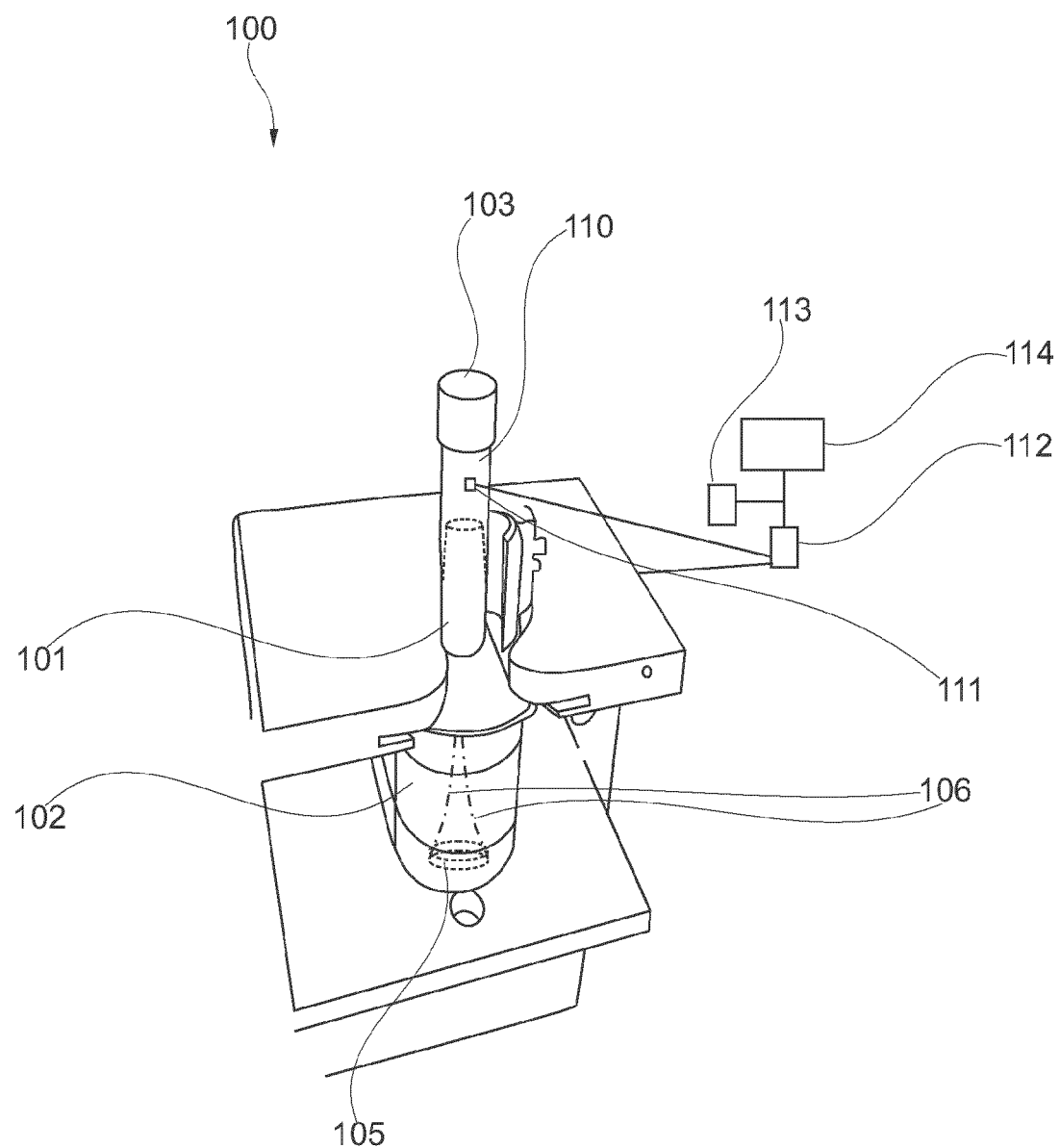
FIG. 1 shows a schematic image of a device for irradiating a sample with focused acoustic energy to treat the sample according to an exemplary embodiment of the present invention.

Similar or relating components in the several figures are provided with the same reference numerals. The view in the figure is schematic and not fully scaled.

Figure 9:
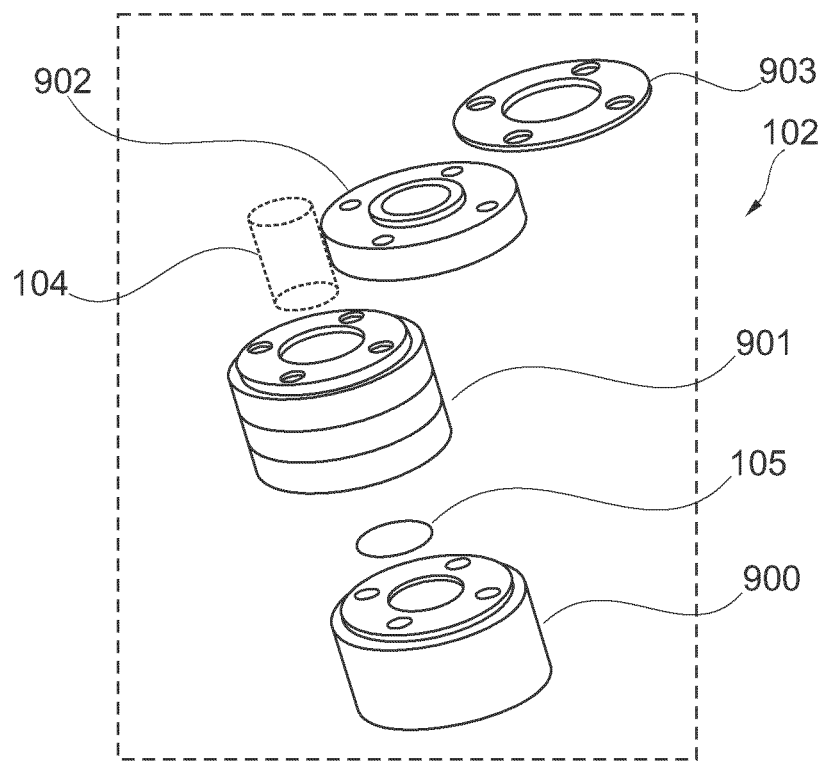
FIG. 9 shows a schematic image of several components of an instrument according to an exemplary embodiment of the present invention.

FIG. 1 shows a device 100 for irradiating a sample 101 with focused acoustic energy to treat the sample according to an exemplary embodiment of the present invention. It can clearly be seen that the device has several components being an instrument 102, a cartridge 103, and a source 105 (shown only with dashed lines) for generating the acoustic energy. Furthermore, a schematic drawing of the propagation path 106 (dashed dotted lines) of the acoustic energy starting at the source 105 and ending at the sample 101. Thereby the cartridge has a chamber 110 for receiving the sample 101. Inside of the shown instrument 102 a full solid coupler (not shown) 104 is provided in order to generate a propagation path without non-fluidic matter. Thereby the source 105 and the full solid coupler 104 are located inside of the instrument 102 and thus cannot directly be seen. Furthermore the instrument 102 and the cartridge 103 are adapted for inserting the cartridge into the instrument wherein the cartridge and the instrument are separable. It shall be noted that the hidden components like the source, the lens, the full solid coupler and the acoustic window can be seen on the following FIG. 9 showing an exploded view and FIG. 2 respectively.

Additionally a detection unit 111, e.g. a sensor, is shown inside of the cartridge in order to do measurements on the sample after or before a possible treatment by the focused acoustic energy. Furthermore a processor for coordinating a treatment protocol 112 is shown which is linked with the detection unit 111 and which is also connected to a display 114 and a data processor 113. The processor 112 for coordinating a treatment protocol is connected to the device 100 and is further connected to the detection unit 111. Thus the processor 112 is enabled to control this complete-in result-out system in which in a fully automated way a treatment of a sample by means of focused acoustic energy especially by HiFu can be combined with analysis and measurements as for example optical measurements, magnetic measurements, thermal measurements, electrical measurements, chemical measurements, sonic measurements and any combinations thereof.

Due to the use of HiFu and the corresponding short wavelength (compared for example to known ultrasound applications operating in the 20 kHz-100 kHz range) the size of focal region can be decreased and thus a miniaturization of the whole molecular device is possible. This is a highly important advantage of the shown embodiment of the present invention with for example hospital or lab requirements to have real small size systems because of the very limited space available in these surroundings. Furthermore, the combination of the functionalities treatment, pretreatment, lysis and previously or subsequently done measurements may reduce the costs and time of such a sample treating or molecular diagnosis.

Additionally it may be possible to provide as such a device 100 with a multi-focality setup. Thereby the device generates at least two different focal regions at the sample 101. This may be done by at least two different sources, a single source and a hybrid lens, or a single source with different roughness stones. Furthermore a combination of these possibilities is also possible.

Furthermore this device 101 may be used to reduce the viscosity of a sample by means of the focused acoustic energy especially by using HiFu.

In addition to that the device makes it possible to combine in one single chamber 110 pretreatment and/or incubation and/or lysis by means of focused acoustic energy originating from only one single source 105. Especially a HiFu application is possible. Thereby pretreatment and lysis may comprise different functionalities that have been described in previous sections. This may reduce costs and time of such a sample treating or molecular diagnosis and also the space claimed of the device may be reduced due to the integration of both functionalities into one chamber. Furthermore the technical complexity of the device may be reduced.

A pretreatment method or a lysis method may be processed or carried out by means of the focused acoustic energy, especially by HiFu and thus by the acoustic source or transducer generating the HiFu spot at the position of the sample yielding to a pretreatment and/or lysis of the sample. But also other devices that may be integrated into the molecular diagnostic device and that are necessary to carry out the method may generate the desired method. For example an additional heating device, cooling devices, or reagent applicator (dispenser) with supply lines may be integrated in the molecular diagnostic device to cause incubation with an additional reagent at elevated temperature.

A reagent may for example be lysozyme enzyme which may first be mixed and subsequently incubated at 37 C. Especially mixing, circulation, liquefaction and homogenation may be done by means of the irradiation of the sample with HiFu.

Furthermore also lysis of micro-organisms like e.g. gram-negative and gram-positive bacteria, fungi and yeast may be done by means of HiFu with the device 100 shown in FIG. 1. Lysing may further comprise incubation of the sample with a reagent at room temperature or elevated temperature. Reagents may for example be GuHCl/prot K which is first mixed and subsequently incubated at approximately 56° C. and optionally cooled down to environmental temperature or GuSCN which is first mixed and subsequently incubated at approximately 70° C. and optionally cooled down to approximately 25° C.

Optionally the chamber has at its outlet a filter or in its outlet channel a filter to assure that debris is not transported to the extraction functionality of the cartridge.

Figure 2:
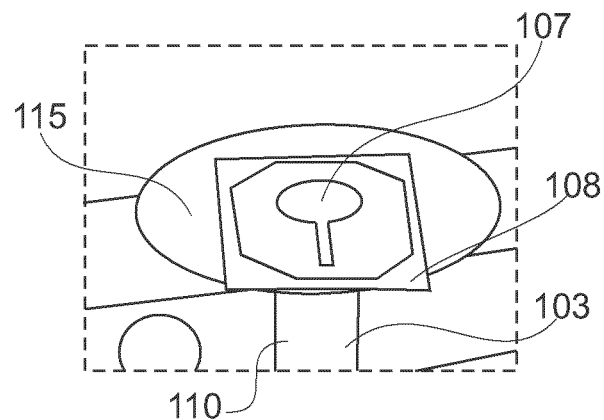
FIG. 2 shows a schematic image of a cartridge having an acoustic window according to an exemplary embodiment of the present invention.

FIG. 2 shows an acoustic window 107 of the cartridge 103 wherein the acoustic window is made of a flexible material which is shown as a plastic foil 108. It can be seen that the circular-shaped acoustic window 107 that is shown in a bottom view is covered by the plastic foil 108 being the interface medium that may adapt itself to the shape of firstly the cartridge 103 and secondly to a full solid coupler or source may be brought in contact with the plastic foil directly on the shown surface 108. 115 shows the bottom part of the cartridge on which a flexible foil is e.g. laser welded.

Figure 3:
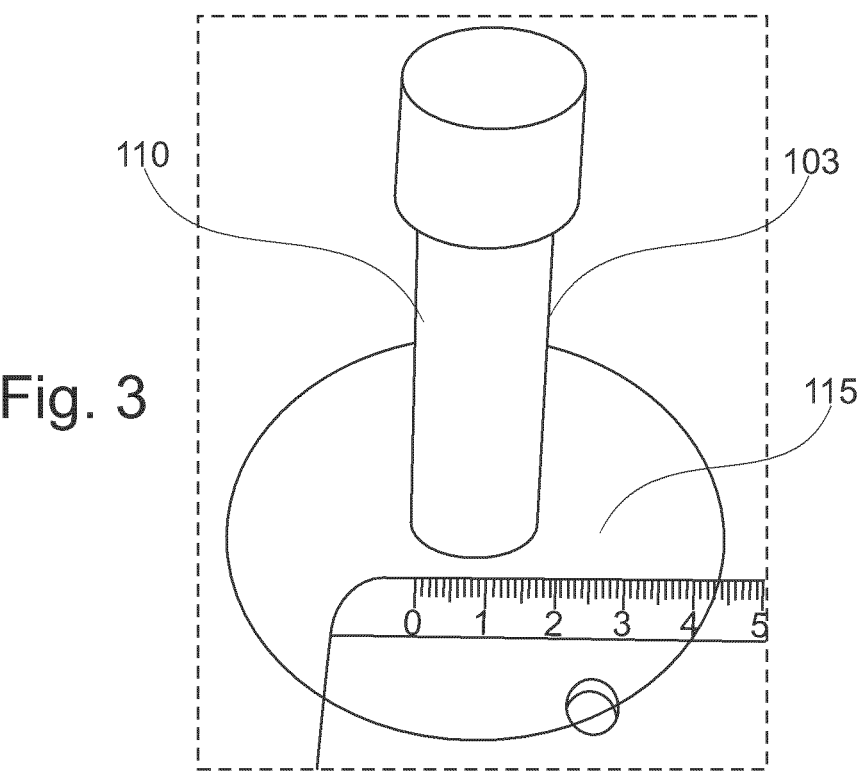
FIG. 3 shows a schematic image of a cartridge according to an exemplary embodiment of the present invention.

FIG. 3 shows the cartridge 103 with the chamber 110 in its normal or working orientation which is a 180° rotation compared to FIG. 2. In other words, FIG. 2 shows the bottom part 115 of the cartridge with its bottom side and FIG. 3 shows the cartridge with the bottom part 115 from the upper side. The shown cartridge and foil clamp can then together as one unit be inserted into the device 100 of FIG. 1 and can be pushed on top of the instrument 102. This inserting process will form a propagation path for transmitting the acoustic energy from the source 105 (shown with dotted lines) in FIG. 1 to the sample 101 in FIG. 1.

Figure 4:
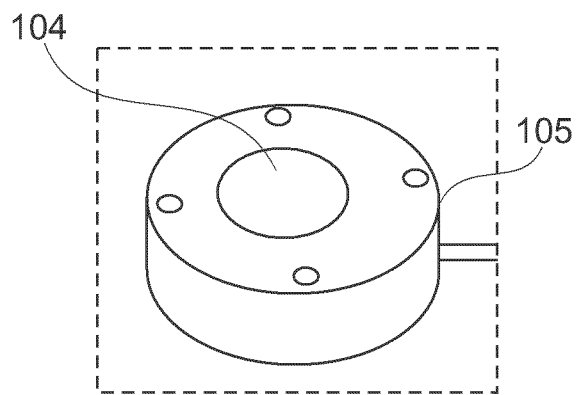
FIGS. 4 to 8 show schematic images of sources of a device according to an exemplary embodiment of the invention.

FIG. 4 shows an example of a possible source used in a device according to an exemplary embodiment wherein a source 105 and a coupler 104 is shown wherein the here shown example is a polymer coupler.

Figure 5:
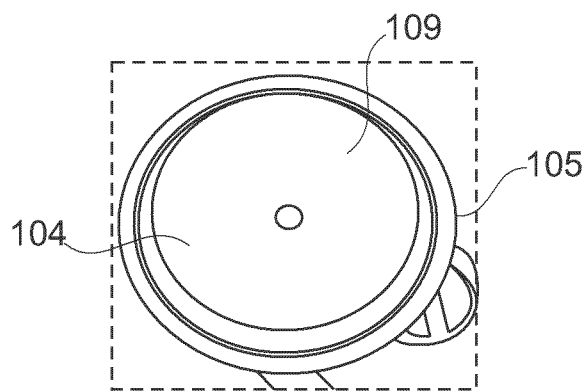

FIG. 5 shows another example of a source creating the focused acoustic energy especially HiFu wherein the source 105 may be a piezo transducer and a metal lens 109 is fixed on top of that for example flat transducer. Additionally a coupler 104 is provided for example a polymer coupler.

Figure 6:
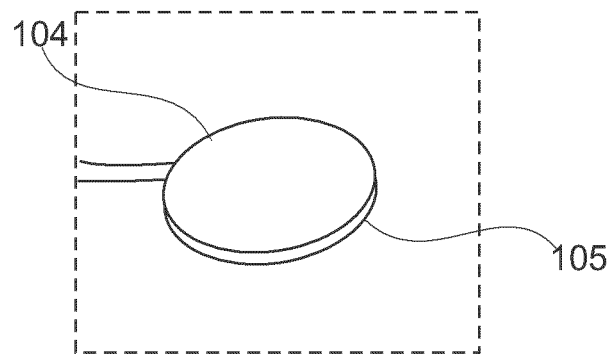

In contrary to that FIG. 6 shows a polymer coupler configuration in which a curved source 105 is combined with a polymer coupler 104. In addition to that for example a lens may be located on top of the polymer coupler being provided with another for example polymer coupler on top of the lens to provide for an efficient dry coupling towards the cartridge.

Figure 7:
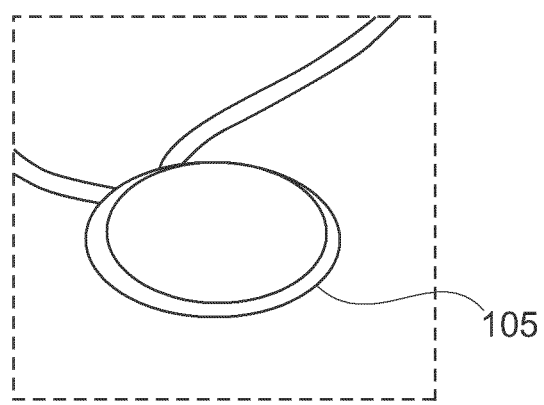

FIG. 7 shows a piezo configuration in which a flat piezo transducer working as a natural focusing source 105 can be seen. Additionally a very thin polymer layer is applied to modify the roughness of the surface to promote efficient dry coupling. In addition to that the electric leads are also shown.

Figure 8:
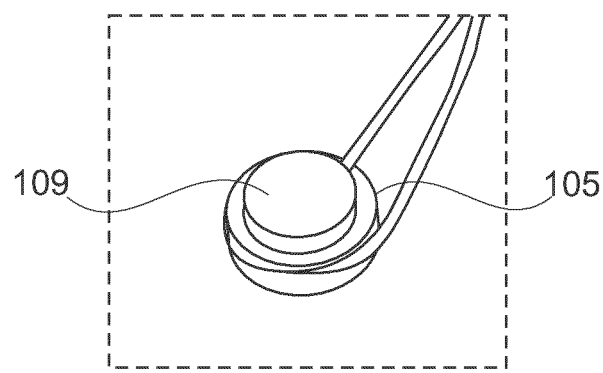

FIG. 8 shows another possible configuration of the source components in which a metal lens 109 is directly contacted to the flat transducer working as a source 105. As will be later on seen in FIGS. 10 to 14 any combination of these configurations is possible which leads to a wide spectrum of applications.

FIG. 9 shows an exploded view of an instrument 102 comprising a heat sink 900, different housing rings 901 partially building up the housing for the full solid coupler 104 that might e.g. be a polymer based material or a solid gel, an additional ring 902. Furthermore the source 105 is shown as a piezo transducer. Additionally the full solid coupler 104 is denoted with dotted lines. These elements may be part of the instrument 102 and they may build a receiving component that by inserting a cartridge on top of the foil clamp 903 creates a propagation path that only consists of non-fluidic matter. The elements 901, 902 and 903 are part of the housing of the coupler, too. The housing is made such that the height of the coupler could be modified by choosing number of housing rings 901. The foil clamp 903 is clamped to the foil (not depicted) which is used to cover the coupler.

Figure 10:
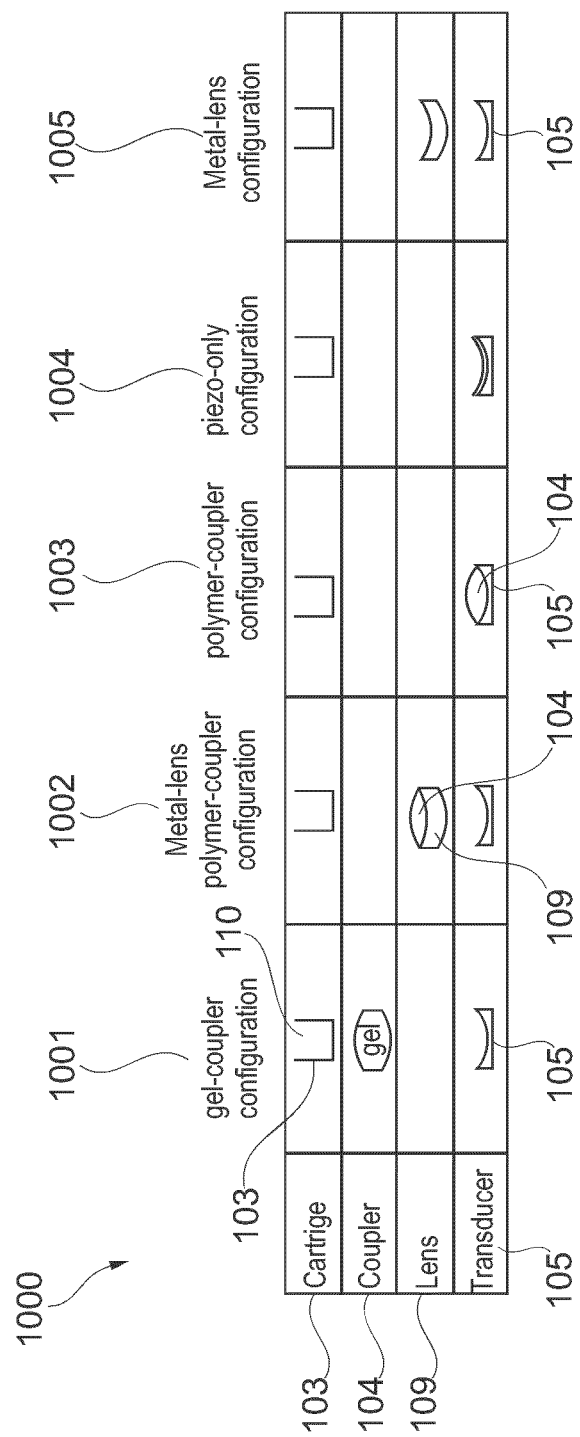
FIGS. 10 to 14 show exemplary overviews of possible configurations of a device according to exemplary embodiments of the present invention.
Figure 11:
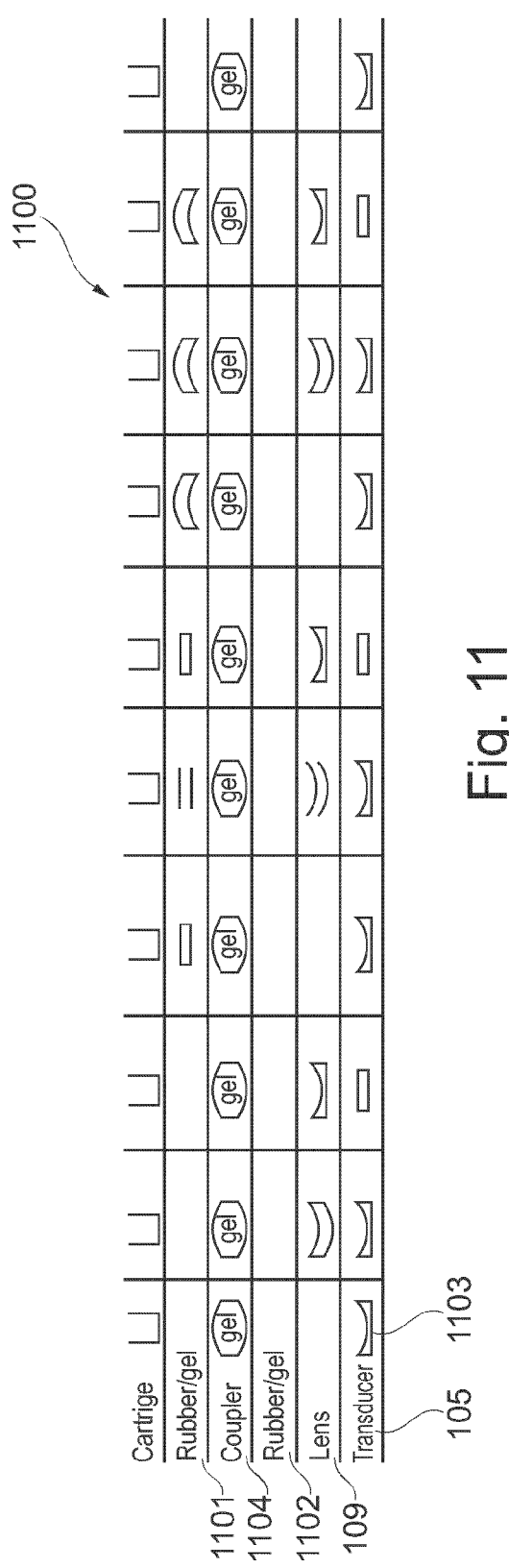
Figure 12:
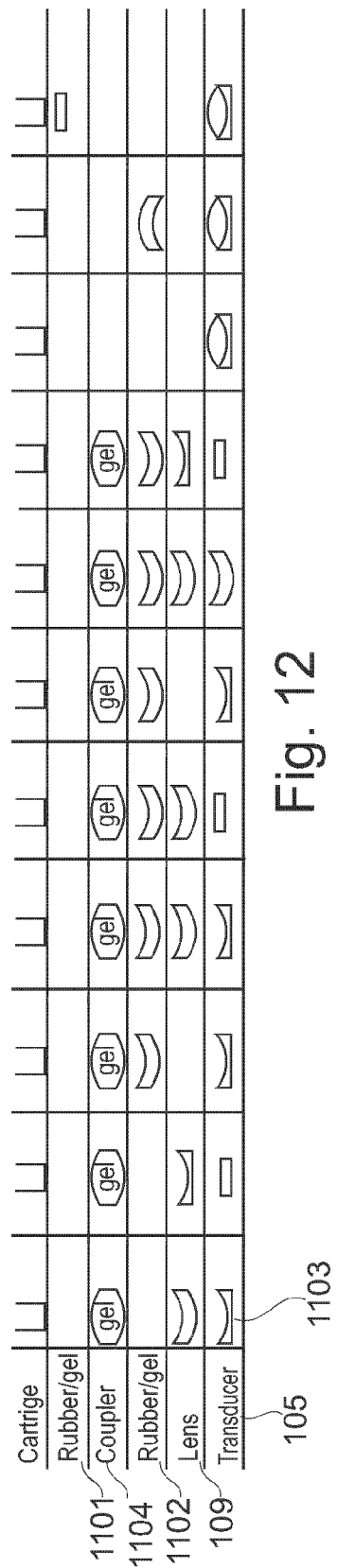
Figure 13:
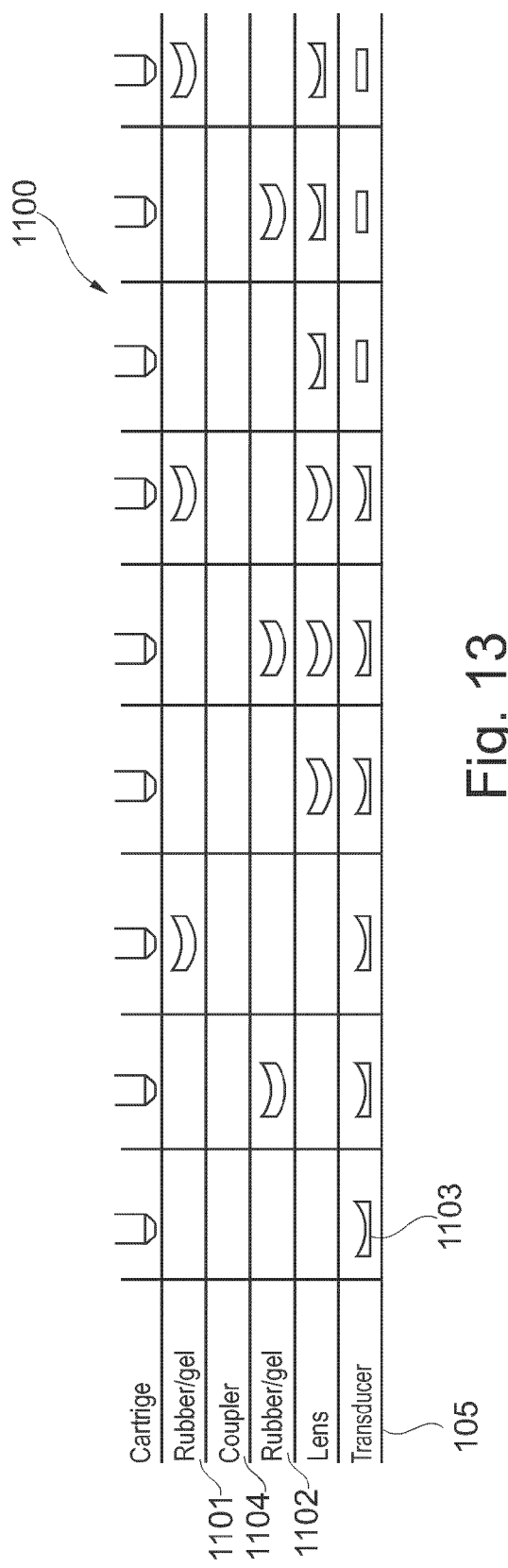
Figure 14:
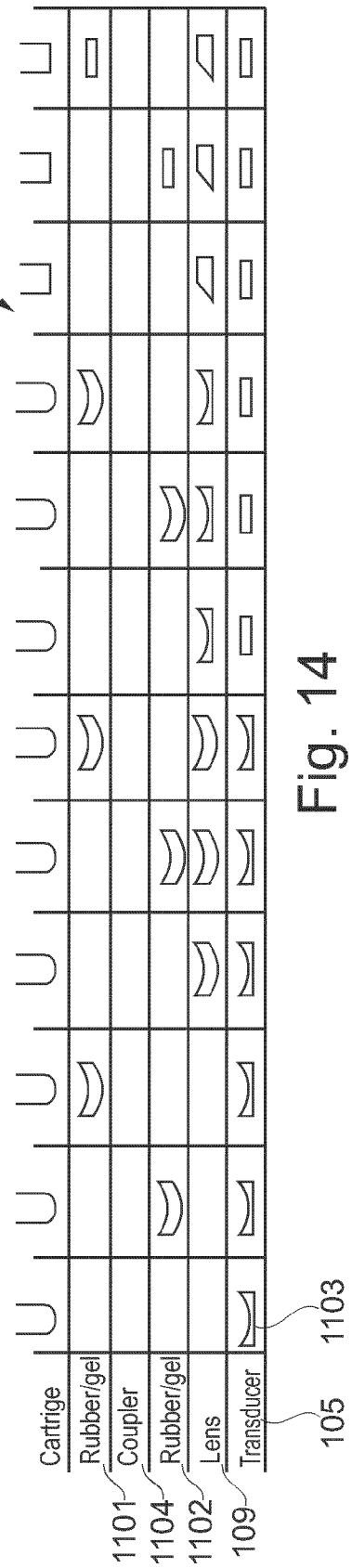

FIG. 10 shows an overview of combinations of possibilities to create dry coupling. Thereby the first row gives information about the setup of the cartridge 103, the second row gives information about the setup of the coupler 104, the third row gives information about the setup of the lens 109 and the fourth row gives information about the setup of the source or transducer 105. It can be seen that five different configurations are shown as examples. 1001 shows a solid gel coupler configuration wherein 1002 shows a metal lens polymer coupler configuration and 1003 describes a polymer coupler configuration. 1004 describes a solution for the dry coupling where a piezo only configuration (wherein the piezo has a thin polymer layer to modify the roughness surface of the transducer) is used and 1005 describes how a metal lens configuration may be set up in order to reach dry coupling. 1001 shows that a source may be shaped like a lens and thus defines the generation and the focusing of the acoustic energy. Furthermore shown in column 1002 the lens may be physically combined for example may be glued together with the solid coupler 104. Furthermore the full solid coupler 104 may be directly attached to the source 105 as shown in column 1003. But also a direct contact between the cartridge and the piezo source is possible as shown in 1004. Additionally the metal lens configuration describes that at a curved shaped source 105 can be attached a biconcave shaped lens e.g. a metal lens.

Other setup possibilities may be shown in the detailed overviews 1100 within the FIGS. 11, 12, 13 and 14. These overviews are more detailed than FIG. 10 because two additional rows are inserted in order to distinguish between the fact whether a component is part of the cartridge, is part of the source (which means is part of the instrument) or is a physically separated component.

It shall explicitly be noted that any shown and described component may be part of the transducer, of the cartridge or may be a physically separated component. In addition to that any combination of components may be used in order to separate different functionalities. For example a thin foil, having a high flexibility may be used to adapt the shape of a transducer. In combination with a full solid coupler having less flexibility but lower attenuation than the foil, this corresponds to the separation of the functionalities attenuation and flexibility. This may lead to an advantageous combination of different components to achieve efficient dry coupling.

Row 1101 describes, if there is an entry, that the full solid coupler is part of the cartridge. In contrary to that 1102 describes the fact that the full solid coupler is part of the source and thus part of the instrument. Also both possibilities may be arranged at an device simultaneously. As a third possibility 1104 describes that the full solid coupler is a physically separated component being inserted into the propagation path. Again it can be seen that a combination of lens and source 1103 may be provided. As can be seen from FIGS. 11 to 14 a huge variety of setup possibilities for the dry coupling of the device using for example HiFu is possible.

FIG. 15 shows exemplary electronic components 1500 being used to generate the focused acoustic energy. Thereby a possible function generator, a power amplifier, a scope and an ultrasonic transducer are connected together in order to create the acoustic field. After having focused the emitted acoustic energy it impinges the sample and causes different sono-chemical or sono-physical reactions. This is the treatment of the sample caused by device. In other words FIG. 15 shows a configuration of a lab setup to generate and investigate the setup performance. An industrial device may not include a scope and the function generator and the amplifier may be embodied in specific and custom made electronics.

FIG. 16 shows a possible treatment protocol for applying pretreatment and lysis in one single chamber by only one single source. Treatment protocol 1600 has several steps for example the protocol starts with a HiFu pretreatment of the sample 1603, subsequently a mixing 1604 is applied to the sample wherein afterwards an incubation with different matter 1605 is possible. Subsequent additional mixing and incubation steps are possible. These different functionalities created or caused by the acoustic energy due to sono-chemical or sono-physical interactions are all part of the pretreatment 1601. Subsequently a lysis 1602 is possible within the same single chamber and can be caused by the same single source that has been processed the pretreatment. As possible steps mixing and incubations may be mentioned. But also special HiFu lysis 1606 and additional filter steps 1607 are possible. Thereby reference sign 1608 describes any sample with a target material to be detected, e.g. feces, blood, urine, sputum, BAL, CSF, tissue, swab or brush. Furthermore a first pretreatment reagent (e.g. chemical compound(s) and/or enzyme(s)) is shown with 1609. A second pretreatment reagent (chemical compound(s) and/or enzyme(s) is shown with reference sign 1610 and 1611 depicts a third pretreatment reagent (chemical compound(s) and/or enzyme(s)). A first lysis reagent (chemical compound(s) and/or enzyme(s)) is shown by 1612. 1613 shows an extraction reagent, e.g. to prepare for DNA binding on silica. The shown figure is only an exemplary embodiment and a filter does not have to be inside the lysis chamber.

Figure 17:
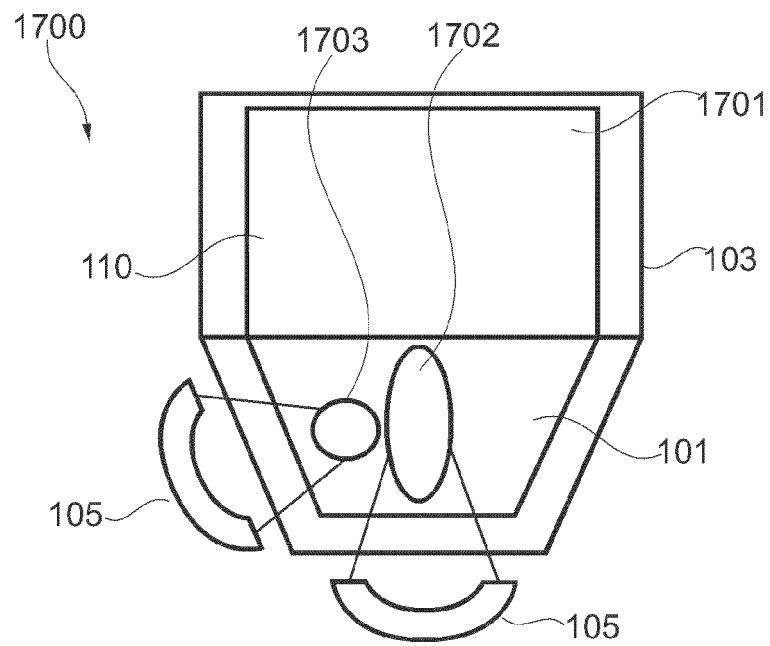
FIGS. 17 to 19 show schematic images of devices generating multi-focality to the sample according to an exemplary embodiment of the present invention.

FIG. 17 shows a multi-focality setup 1700 of the device according to another exemplary embodiment of the invention. It can be seen that the cartridge 103 having a chamber 110 with a sample 101 also features the possibility to have an air volume 1701 above the sample. Furthermore two different sources 105 are applied in the setup in order to generate a first focal region 1702 and 1703 showing a second focal region. Furthermore the acoustic window of the cartridge should have a low attenuation and minimal thickness to avoid heating of the material and to realize a high intensity in the focal regions. For mass production an injection moldable polymer is preferred. It may be preferred that no contact is made of the focal regions with the walls of the chamber. At high intensities this may result in melting of the wall. It may further be desired that the transducer with the large focal zone 1702 is placed opposite to the air volume 1701. This results in optimal mixing and circulation and may have lower risk on melting the chamber wall.

Figures 18A, 18B:
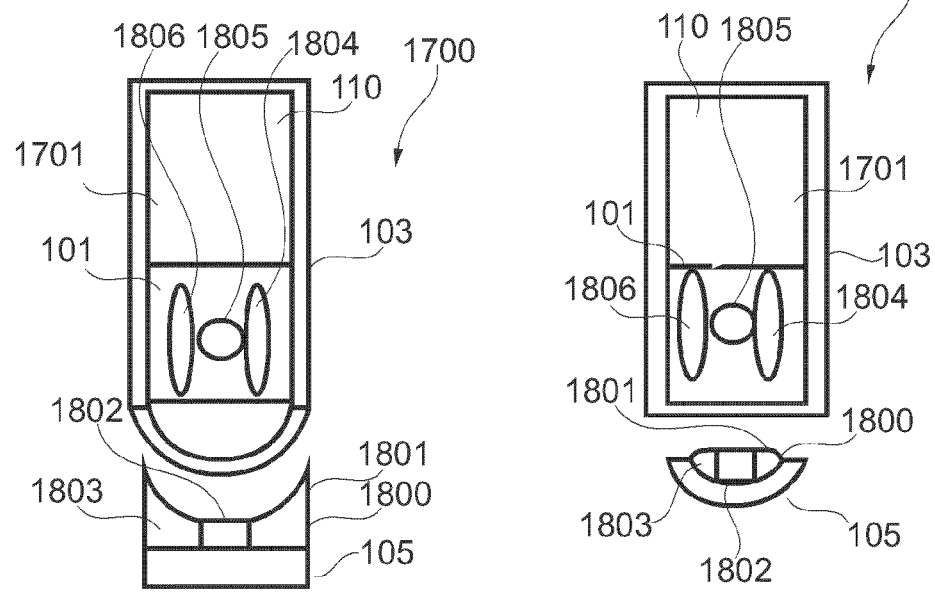

FIGS. 18a and 18b show multi-focality of the device working for example in the HiFu range, may be generated by only one single source. Thereby FIG. 18a shows a multi-focality setup 1700 with a hybrid lens 1800 having a first emitting zone 1801 and a second emitting zone 1802 and a third emitting zone 1803. It is also possible that in a concentric setup the first and the third emitting zones are equal. It can further be seen, that in the sample 101 three different focal regions 1804 to 1806 are generated. In a concentric setup it is thus the case that 1804 and 1806 describe the same focal region having a ring-like shape around the second focal region 1805.

It can be seen that the source 105 may be of a flat shape and the hybrid lens 1800 is attached to the source.

FIG. 18b shows a multi-focality setup 1700 wherein the hybrid lens 1800 has got a shape that is adapted to the shape of the curved source 1500. In FIG. 18b the hybrid lens has three emitting zones and three focal regions originating from the three emitting zones. The different emitting zones may consist of different focusing material. For example, the outer material forming zone 1801 and 1803 may be of moderately focusing outer material wherein the inner material forming the zone 1802 may be a highly focusing material. The segmented lens 1800 thus comprises highly focusing material and moderately focusing material. This may be the case for FIG. 18b. These different focal regions may enable a user to process different functionalities like mixing and lysing simultaneously by only using one single source. This may reduce the times of for example a molecular test and furthermore costs and space requirements may be reduced as only one single source is needed. Additionally technical problems and maintenance costs are reducible.

Thereby the distribution of the differently focusing materials can be adapted the desired treatment, lysis or analyzing application. Thus no specific material distribution within the hybrid lens or segmented lens is excluded by this exemplary embodiment of the invention.

The following paragraph relates to modeling of a combination comprising a flat transducer and a curved lens to verify the hybrid lens concept. A possible setup may be for example a high impedance material like for example aluminum, a low impedance material like polypropylene taken as a lens material, a lens radius and internal diameter of the chamber like for example 8 mm and polypropylene is taken as chamber wall material with a thickness of 0.5 mm, a fluid height is 35 mm and the frequency for the modeling is 1 MHz and prescribed pressure piezo is 1.000 Pa. The results of the modeling disclosed that the maximum pressure along the central axis of symmetry remains at a very constant high level when going from a complete high impedance material (aluminum) to increasing segment sizes of low impedance material like polypropylene. In other words, the pressure remains at the level sufficient high to obtain lysis. Secondly the results revealed that a minimum and maximum pressure conditions are created outside the central axis of the chamber when the polypropylene segment size is sufficiently large to create mixing. Effective working of the hybrid construction is achieved when the high index material (aluminum for instance) is typically between ⅕ and ½ of the total lens when a low index material is a low dissipation plastic. Thus a hybrid lens is an option to generate multifocal acoustic energy especially multifocal HiFu from a single piezo element. This solution could be used for HiFu across dry interfaces as well as for liquid or hydrogel coupling and direct contact with the fluid.

Figure 19:
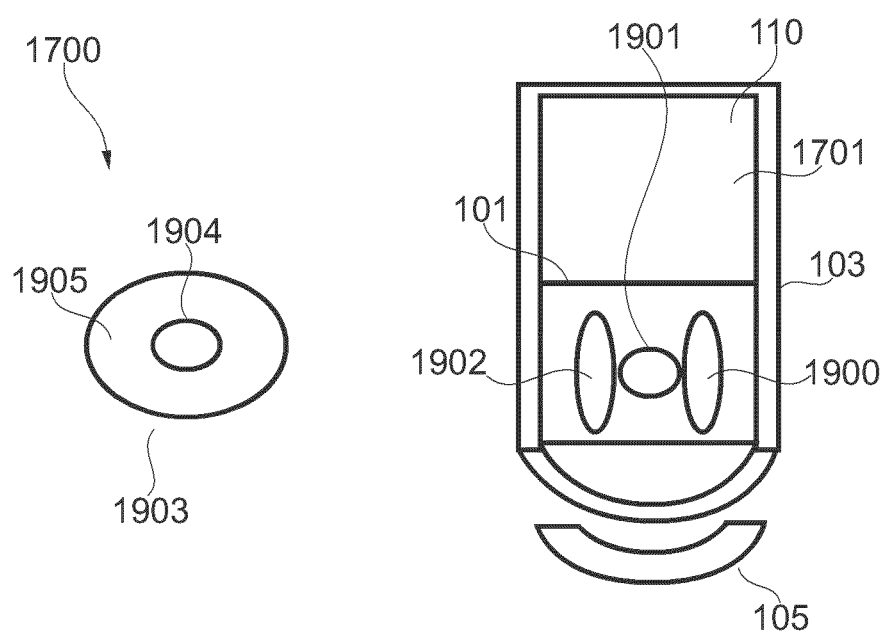

FIG. 19 shows a multifocal setup 1700 wherein a source 105 has different surface roughness zones. 1903 shows a top view of the circular source 105 having a first surface roughness zone 1904 and a second surface roughness zone 1905 yielding to multi-focality. It can be seen that the first focal region 1900 and the second focal region 1901 are different from each other. Here the third focal region 1902 is the same as the first focal region 1900 because the second roughness zone 1905 is a ring-shaped surface that yields to a ring-shaped focal region 1900 and 1902 around the second focal region 1901. Due to different roughnesses of the surfaces a different coupling to material transmitting the acoustic energy is given. Therefore, different roughnesses yield in different focal regions.

It shall explicitly be noted that the multi-focality due to different surface roughnesses may not be used with the dry coupling features of the present invention and may be applied independently on a device for irradiating a sample with multi focused acoustic energy to treat the sample.

For example, in the range of 1 to 2 MHz the effect may be moderate for a roughness of 10 µm and may be significantly higher for a roughness of 50-80 µm. Thus, a curved transducer with rough and smooth segments is an option to generate multifocal HiFu from a single piezo element. Compared to different solutions with lenses or a plurality of sources this embodiment may be simpler.

Figure 20:
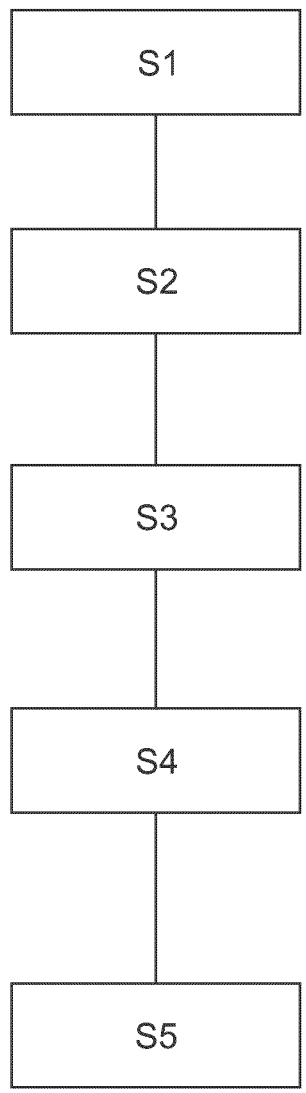
FIG. 20 shows a flow diagram representing a method according to an exemplary embodiment of the present invention.

FIG. 20 shows a flow diagram describing a method for irradiating a sample with focused acoustic energy to treat the sample wherein the following steps are comprised and for an instrument S1, providing for a cartridge S2, providing for a full solid coupler S3, providing for a source for generating the acoustic energy S4. Furthermore inserting the cartridge into the instrument S5 wherein the cartridge has a chamber for receiving the sample and wherein due to the inserting of the cartridge into the instrument a complete dry coupling of the acoustic energy between the source and the cartridge is provided. Furthermore the cartridge and the instrument are separable.

Figure 21:
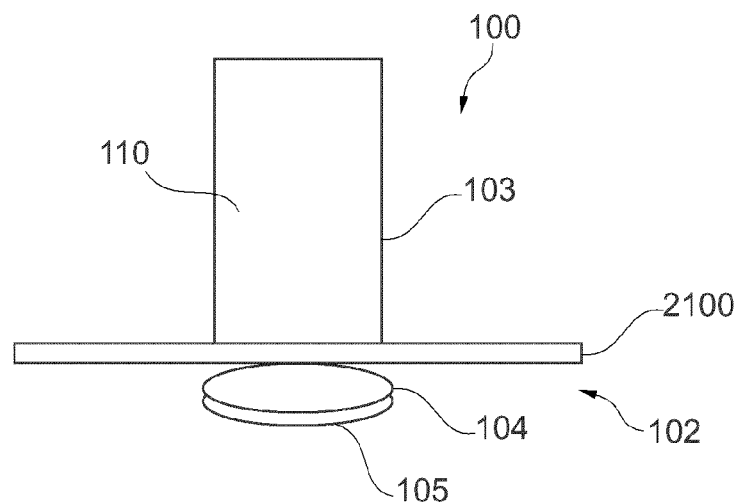
FIG. 21 shows a schematic image of a device for irradiating a sample with focused acoustic energy to treat the sample according to an exemplary embodiment of the present invention.

FIG. 21 shows a schematic drawing of an instrument device comprising a transducer 105, a full solid coupler 104, and a cartridge 103 having a chamber 110 for a sample to be treated with e.g. HIFU by the instrument 102. The bottom 2100 of the cartridge has an acoustic window made out of a foil.

Figure 22:
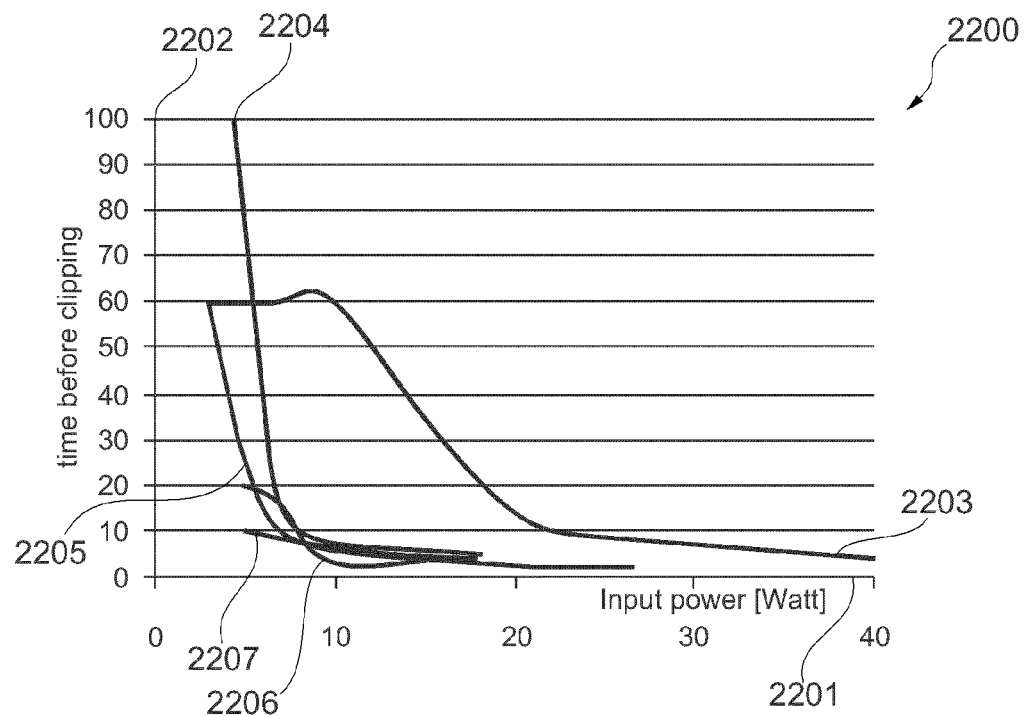
FIGS. 22 and 23 show a diagrams of results obtained with a device for irradiating a sample with focused acoustic energy to treat the sample according to an exemplary embodiment of the present invention.

FIG. 22 shows a diagram 2200 in which the advantages of a full solid coupler with a sufficiently high glass transition temperature $T_g$ are illustrated. It can be seen from the graphs 2203-2207, that a full solid coupler with higher glass transition temperature $T_g$ provides for less attenuation of the ultra sound energy within the full solid coupler. These results shall be describe in detail hereinafter.

The x-coordinate 2201 depicts the input power that is provided to the source 105 (not shown) which generates the acoustic energy e.g. the HIFU. The y coordinate depicts the so called clipping time. This is the time between the source generating e.g. the HiFu is switched on and the complete disappearance of the fountain (clipping). This fountain generation has been described above. It is created by the HIFU waves and is used to reduce the power threshold at which cavitation in the sample sets in. The fountain is consisting of the sample material (e.g. a liquid). As the generation of such a fountain depends on the acoustic energy that is transmitted through the full solid coupler to the sample the disappearance of the sample means a reduction of transmitted acoustic energy. Different materials with different glass transition temperatures are observed within the test of the results shown in FIG. 22.

In other words clipping is taken as a measure for the development of the attenuation or absorption with time of the observed full solid coupler material. Results for a variety of materials and thicknesses are presented in FIGS. 22 and 23.

Thereby FIG. 22 shows results from a 3 mm thick silicon 601 coupler 2203 having a glass transition temperature of 60° C. 2204 depicts the results from a 3 mm thick full solid coupler made out of epotek 301 having a glass transition temperature $T_g$ of approximately 60° C. 2205 depicts the results of a 6 mm thick silicon 601 coupler having a glass transition temperature of 60° C. 2206 depicts the results of a full solid coupler that is 1 mm thick and made out of polypropylene (PP) having a glass transition temperature $T_g$ of approximately −18° C. 2207 depicts the results of a full solid coupler made out of 5 mm thick epotek 301 having a glass transition temperature of approximately 60° C. All examples have cure temperatures of 60 C except PP.

FIG. 22 shows that PP is even at moderate intensity a rather poor performer. Attenuation of both epoxy and silicone increases as expected with thickness of the full solid coupler. Attenuation of epoxy is for silicon lower than for epoxy. For all of these high $T_g$ materials clipping is observed for continuous input power <6 Watt. This power may be insufficient for sample treatment. Thus for broad treatment possibilities of a molecular diagnostic device the invention provides for sufficiently high $T_g$ polymers.

Additional experiments have disclosed that firstly the observed phenomena are not due to a change over time of the transducer. Secondly the effect may be reversible (if the material is not exposed to burn-through intensities). After about 1 min the material is returned to its original state and the experiment could be repeated. This observation suggests a temperature-material property relationship.

Figure 23:
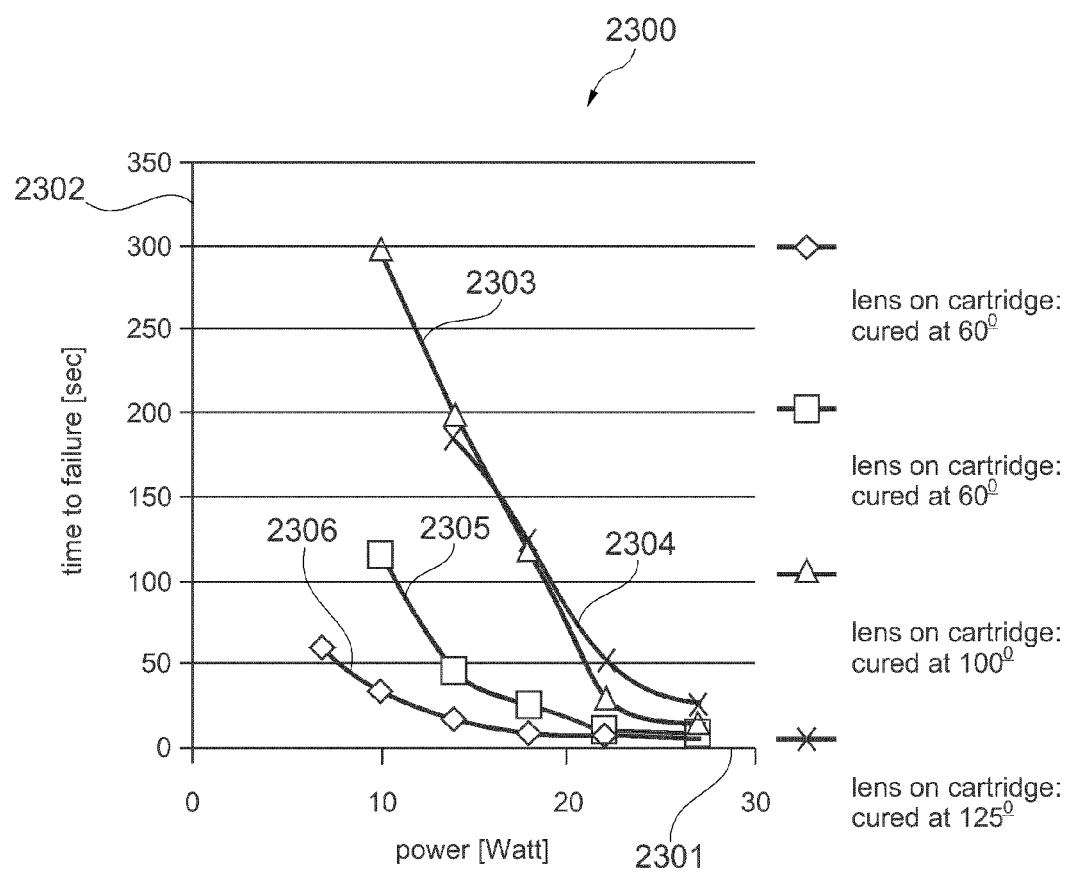

FIG. 23 shows a diagram 2300 in which the effect of the curing temperature of the polymer based material used as a full solid coupler is shown. X-coordinate 2301 depicts the input power and y-coordinate 2302 depicts the time to failure i.e. the clipping time. 2303 to 2306 depict the graphs of the different full solid coupler. 2303 depicts the result of a full solid coupler with the curing temperature $T_c$ is 100° C., 2304 depicts $T_c$ is 125° C., 2305 depicts $T_c$ is 60° C. and 2306 also depicts the results of a coupler with $T_c$ is 60° C. In other words FIG. 23 shows that the effect attenuation is also dependent on the curing temperature. With increasing curing temperature the clipping time increases significantly. An exemplary embodiment of the invention uses this advantage. In other words in general a higher curing temperatures $T_c$ directly translates into a higher glass transition temperature $T_g$.

Additional experiments with the material cured at 60 C have shown that:

Firstly fountain disappeared if water of 80 C or more is used. Secondly with a duty cycle of 20% the clipping time shift to >120 seconds for peak power between 0 W and 65 W (average power 13 W). For a peak power of 90 W (average power 16 W) the clipping time has reduced to 10 seconds.

Possible exemplary equipment devices for these test may be the following: PM5193 Programmable Synthesizer/function generator 0.1 mHz-50 MHz, Amplifier: ENI 240L Power Amplifier 50 dB 20 kHz-10 MHz or AR worldwide KAA204 RF Power Amplifier 50 dB 0.5-100 MHz 200 W, Tektronix TDS3014: Four Channel Color Digital Phosphor Oscilloscope; Agilent 4395A: 10 Hz-500 MHz/10 Hz-500 MHz/10 kHz-500 MHz Network/Spectrum/Impedance Analyzer and HiFu piezo transducer: JR20/60 supplied by Dongfang Jinrong.

In the claims the word "comprising" does not exclude other elements or steps, and the indefinite article "a" or "an" does not exclude a plurality. Reference signs shall not limit the scope of the claims.

LIST OF REFERENCE NUMERALS

100 Device
101 Sample
102 Instrument
103 Cartridge
104 Full solid coupler
105 Source
106 Propagation path
107 Acoustic window
108 Flexible material
109 Lens
110 Chamber
111 Detection unit
112 Processor for coordinating a treatment protocol
113 Data processor
114 Display
115 Bottom part
900 Heat sink
901 Housing rings
902 Additional ring
903 Foil clamp 1000 Overview of combination possibilities to create dry coupling
1001 Solid gel coupler configuration
1002 Metal lens polymer coupler configuration
1003 Polymer coupler configuration
1004 Piezo only configuration (wherein the piezo has a thin polymer layer to modify roughness surface)
1005 Metal lens configuration
1100 Detailed overviews of combination possibilities to create dry coupling
1101 Row describing that the full solid coupler is part of the cartridge
1102 Row describing that the full solid coupler is part of the instrument
1103 Component combining the functionality of a lens and a source (curved source)
1104 Row describing that the full solid coupler is a physically separated component
1500 Electronics being used to generate the focused acoustic energy
1600 Possible treatment protocol for applying pretreatment, incubation and lysis in one single chamber by one single source
1601 Pretreatment part of the protocol
1602 Lysis part of the protocol
1603 HiFu pretreatment
1604 Mixing
1605 Incubation
1606 HiFu lysis
1607 Filtering
1608 Sample with a target material to be detected
1609 First pretreatment reagent
1610 Second pretreatment reagent
1611 Third pretreatment reagent
1612 First lysis reagent
1613 Extraction reagent
1700 Multi-focality setup
1701 Air volume above the sample
1702 First focal region
1703 Second focal region
1800 Hybrid lens
1801 First emitting zone of the hybrid lens
1802 Second emitting zone of the hybrid lens
1803 Third emitting zone of the hybrid lens
1900 First focal region
1901 Second focal region
1902 Third focal region
1903 Top view of source 105 with different roughnesses zones
1904 First roughness zone of the source
1905 Second roughness zone of the source
S1 Providing for an instrument
S2 Providing for a cartridge
S3 Providing for a full solid coupler
S4 Providing for a source for generating the acoustic energy
S5 Inserting the cartridge into instrument

What is claimed is:

1. A device for irradiating a sample with focused acoustic energy to treat the sample, the device comprising:
an instrument;
a cartridge having a chamber for receiving the sample, wherein the instrument and the cartridge are adapted for inserting the cartridge into the instrument, and wherein the cartridge and the instrument are separable;
a single source for generating acoustic energy; and
a fully solid coupler providing a completely dry coupling of the acoustic energy between the source and the cartridge,
wherein at least two different focal regions are generated by an element selected from the group consisting of: the source and a hybrid lens for focusing the acoustic energy onto the sample, the source with different roughness zones, the source being excited differently at different positions of the source, and any combination thereof.

2. The device according to claim 1, wherein the source is configured so that the acoustic energy is high intensity focused ultra sound (HiFu).

3. The device according to claim 1, wherein the instrument and the cartridge are arranged in combination in such a way, that by inserting the cartridge into the instrument a propagation path for transmitting the acoustic energy from the source to the sample is formed, and wherein the propagation path consists only of non-fluidic matter.

4. The device according to claim 1, wherein the fully solid coupler comprises a material selected from the group consisting of solid gel, rubber, elastic foil, polymer based material, thermoplastic polymers, polymer having a low acoustic attenuation characteristic, metal, semiconductor, ceramic, polypropylene, aluminum, and a stack of these materials.

5. The device according to claim 1, wherein the cartridge comprises an acoustic window made of a flexible material, and wherein the fully solid coupler is physically contacted with the acoustic window by inserting the cartridge into the instrument.

6. The device according to claim 5, wherein the fully solid coupler has a first contact surface for contacting the acoustic window, the cartridge has a second contact surface for contacting the acoustic window, and at least one of the first contact surface, the second contact surface and the acoustic window has a surface roughness value selected from the group consisting of smaller than 0.5 micrometers, smaller than 1 micrometers, and smaller than 2 micrometers.

7. The device according to claim 3, wherein the propagation path has a gradient of an acoustic impedance that is monotonously decreasing in a direction from the source to the sample.

8. The device according to claim 1, wherein the lens is selected from the group consisting of a lens being a physically separate component placed between the source and the cartridge, a lens being part of the source, the source with a focusing shape being the lens, an array of sources that yield to focused acoustic energy, a lens being part of the cartridge, a lens made out of a polymer having a low acoustic attenuation characteristic, a metal lens, a ceramic lens, a polypropylene lens, an aluminum lens, a hybrid lens, and any combination thereof.

9. The device according to claim 1,
wherein said device irradiates the sample in one single chamber of the cartridge with focused acoustic energy to apply pretreatment and lysis thereto;
wherein the pretreatment is a method selected from the group consisting of mixing with a reagent, circulation, release of a cell, pathogen and matrix from a swab, release of a cell, pathogen and matrix from a brush, liquefaction, incubation of the sample with a reagent at room temperature or elevated temperature, shaking, mixing; stirring, extraction, NA extraction, flow generation, sample homogenation, separating by centrifuging, and any combination thereof, and
wherein lysis is a method selected from the group consisting of mixing with a reagent, circulation, lysis of microorganisms, incubation of the sample with a reagent at room or elevated temperature, and any combination thereof.

10. The device according to claim 1, further comprising at least one of: an extraction unit; a nucleic acid amplification unit; a reagent storage unit; a detection unit a detection unit for applying measurements on the sample wherein the detection unit is for applying at least one measurement to the sample selected from the group consisting of optical measurements, magnetic measurements, thermal measurements, electrical measurements, chemical measurements, sonic measurements, and any combination thereof, wherein the irradiation of the sample with the acoustic energy leads to a treatment of the sample.

11. The device according to claim 1, wherein the fully solid coupler is made out of a polymer based material having a glass transition temperature $T_g$ selected from the group consisting of: $T_g \geq -30°$ C.; $T_g \geq -10°$ C., $T_g \geq -5°$ C.; $T_g \geq 20°$ C.; $T_g \geq 40°$ C.; $T_g \geq 60°$ C.; $T_g \geq 80°$ C.; $T_g \geq 100°$ C.; $T_g \geq 120°$ C.; $T_g \geq 130°$ C.; $T_g \geq 140°$ C.; $T_g \geq 150°$ C.; and $T_g \geq 160°$ C.

12. The device according to claim 11, wherein the polymer based material has been cured at a curing temperature $T_C$ selected from the group consisting of: $T_C \geq 20°$ C.; $T_C \geq 40°$ C.; $T_C \geq 60°$ C.; $T_C \geq 70°$ C.; $T_C \geq 80°$ C.; $T_C \geq 90°$ C.; $T_C \geq 100°$ C.; $T_C \geq 110°$ C.; $T_C \geq 120°$ C.; $T_C \geq 130°$ C.; $T_C \geq 140°$ C.; $T_C \geq 150°$ C.; $T_C \geq 160°$ C.; $T_C \geq 170°$ C.; and $T_C \geq 180°$ C.

13. A cartridge for an instrument for irradiating a sample with focused acoustic energy generated by a single source to treat the sample, the cartridge comprising:
   a chamber for receiving the sample; and
   a fully solid coupler,
   wherein the cartridge is adapted for being inserted in the instrument and for being separable from the instrument, and
   wherein the fully solid coupler provides a completely dry coupling of the acoustic energy between the source and the cartridge when the cartridge is inserted in the instrument, said completely dry coupling providing at least two different focal regions that are generated by an element selected from the group consisting of: the source and a hybrid lens for focusing the acoustic energy onto the sample, the source with different roughness zones, the source being excited differently at different positions of the source, and any combination thereof.

14. A method of irradiating a sample with focused acoustic energy to treat the sample, the method comprising the following steps:
   providing an instrument;
   providing a cartridge having a chamber for receiving the sample, wherein the instrument and the cartridge are adapted for inserting the cartridge into the instrument, and wherein the cartridge and the instrument are separable;
   providing a single source for generating acoustic energy;
   providing a fully solid coupler to provide a completely dry coupling of the acoustic energy between the source and the cartridge,
   wherein the fully solid coupler provides a completely dry coupling of the acoustic energy between the source and the cartridge when the cartridge is inserted in the instrument, said completely dry coupling providing at least two different focal regions that are generated by an element selected from the group consisting of: the source and a hybrid lens for focusing the acoustic energy onto the sample, the source with different roughness zones, the source being excited differently at different positions of the source, and any combination thereof;
   placing the sample in the chamber of the cartridge;
   inserting the cartridge into the instrument; and
   generating the at least two different focal regions with the source for generating acoustic energy.

* * * * *